United States Patent
Pinkowski et al.

(10) Patent No.: US 9,247,948 B2
(45) Date of Patent: Feb. 2, 2016

(54) CHANGE-OUT HANDLE SYSTEM AND MEDICAL INSTRUMENT

(75) Inventors: Wolfhard Pinkowski, Aschheim (DE); Bernhard Uihlein, Dettingen (DE); Dieudonne Mbarga, Achenmuehle (DE); Werner Schwarz, Ruhpolding (DE)

(73) Assignee: Urotech Medizinische Technologie GmbH, Achenmuehle (DE)

( * ) Notice: Subject to any disclaimer, the term of this patent is extended or adjusted under 35 U.S.C. 154(b) by 0 days.

(21) Appl. No.: 13/301,399

(22) Filed: Nov. 21, 2011

(65) Prior Publication Data

US 2012/0088972 A1   Apr. 12, 2012

Related U.S. Application Data

(63) Continuation of application No. PCT/EP2009/009256, filed on Dec. 23, 2009.

(30) Foreign Application Priority Data

May 22, 2009   (DE) .................. 10 2009 022 379

(51) Int. Cl.
| | | |
|---|---|---|
| *A61B 17/00* | (2006.01) | |
| *A61B 17/221* | (2006.01) | |
| *A61B 19/00* | (2006.01) | |

(52) U.S. Cl.
CPC ............ *A61B 17/221* (2013.01); *A61B 19/22* (2013.01); *A61B 19/2203* (2013.01); *A61B 2017/0046* (2013.01); *A61B 2017/00477* (2013.01); *A61B 2019/2242* (2013.01)

(58) Field of Classification Search
CPC ............ A61B 19/22; A61B 19/2203; A61B 2019/2242
USPC ............................................... 606/1
See application file for complete search history.

(56) References Cited

U.S. PATENT DOCUMENTS

| | | | |
|---|---|---|---|
| 2,113,246 A | | 5/1937 | Wappler |
| 4,691,705 A | * | 9/1987 | Okada .......................... 606/127 |
| 5,779,686 A | | 7/1998 | Sato et al. |

(Continued)

FOREIGN PATENT DOCUMENTS

| | | |
|---|---|---|
| EP | 0 943 293 A1 | 9/1999 |
| WO | WO 01/87166 A2 | 11/2001 |

OTHER PUBLICATIONS

International Search Report dated Apr. 16, 2010 with English translation (six (6) pages).

*Primary Examiner* — William Thomson
*Assistant Examiner* — Sebastian X Lukjan
(74) *Attorney, Agent, or Firm* — Crowell & Moring LLP

(57) ABSTRACT

A change-out handle system is provided for releasably coupling two elongated, axially relatively displaceable functional parts to a medical instrument unit. The change-out handle system includes a first and a second handle part disposed axially relatively displaceably, a first coupler for releasably axially rigidly immovably coupling a first of the two functional parts to the first handle part and a second coupler for releasably, axially rigidly immovably coupling the second of the two functional parts to the second handle part. The second handle part has a pass-through opening for passing at least the first of the two functional parts. The change-out handle system can be used, for example, for medical solids trapping instruments.

23 Claims, 15 Drawing Sheets

(56) References Cited

U.S. PATENT DOCUMENTS

| | | |
|---|---|---|
| 6,007,560 A | 12/1999 | Gottlieb et al. |
| 6,053,934 A | 4/2000 | Andrews et al. |
| 6,695,773 B1 * | 2/2004 | Dahlinger .................... 600/119 |
| 6,764,499 B2 * | 7/2004 | Honey et al. ................. 606/207 |
| 2002/0010459 A1 | 1/2002 | Whittier et al. |
| 2002/0026202 A1 | 2/2002 | Honey et al. |
| 2005/0113862 A1 | 5/2005 | Besselink et al. |
| 2005/0182292 A1 | 8/2005 | Suzuki |
| 2005/0251111 A1 * | 11/2005 | Saito et al. ........................ 606/1 |
| 2008/0132940 A1 | 6/2008 | Lavelle et al. |

* cited by examiner

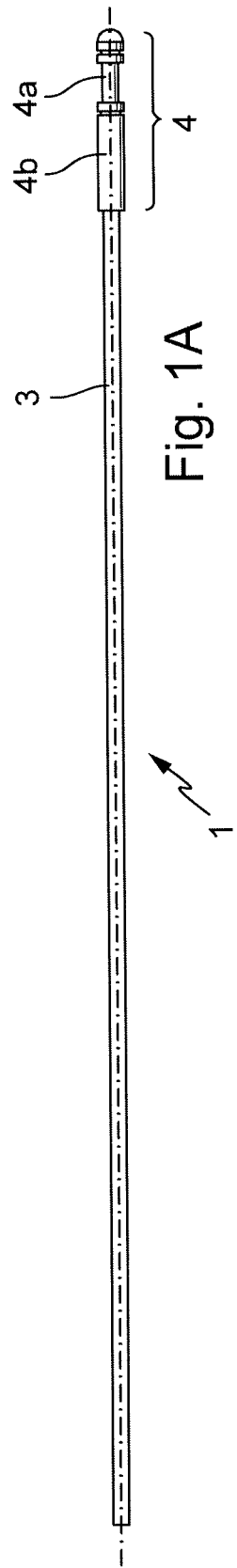
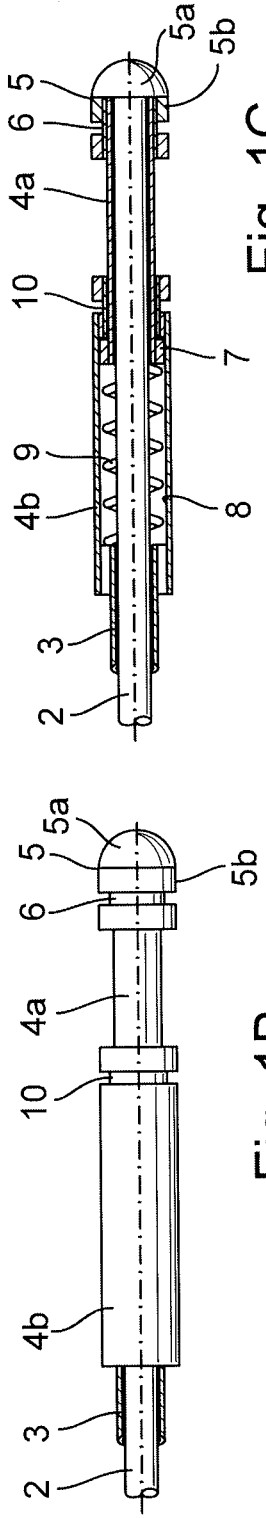
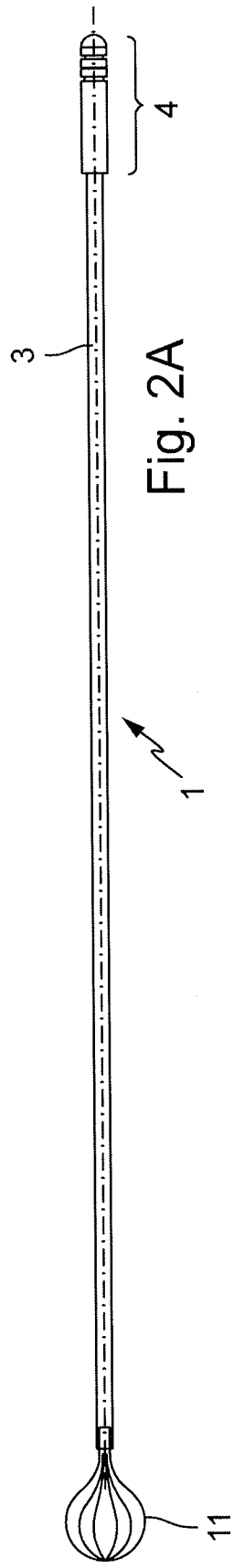
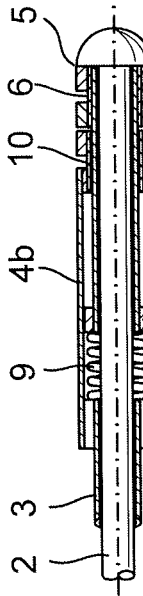
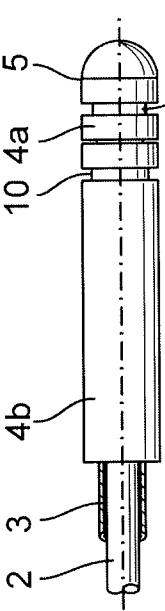

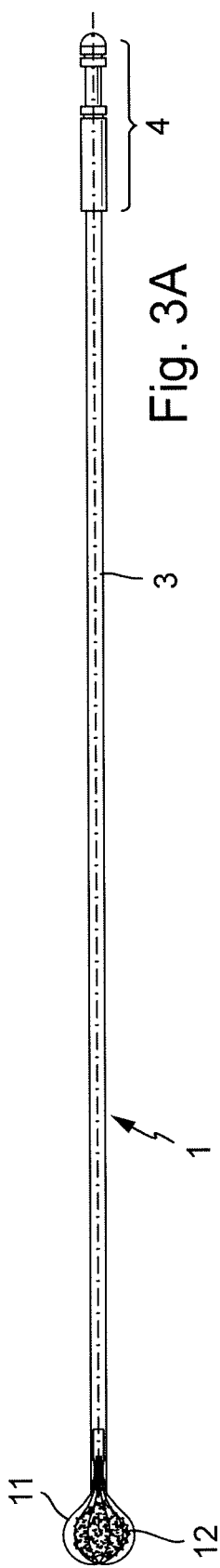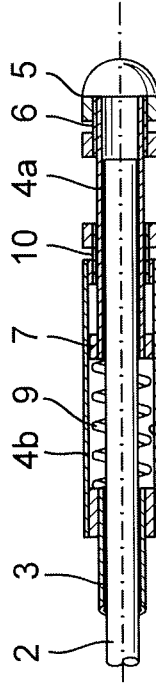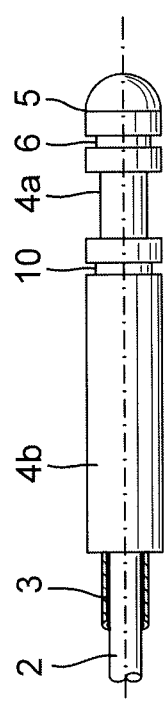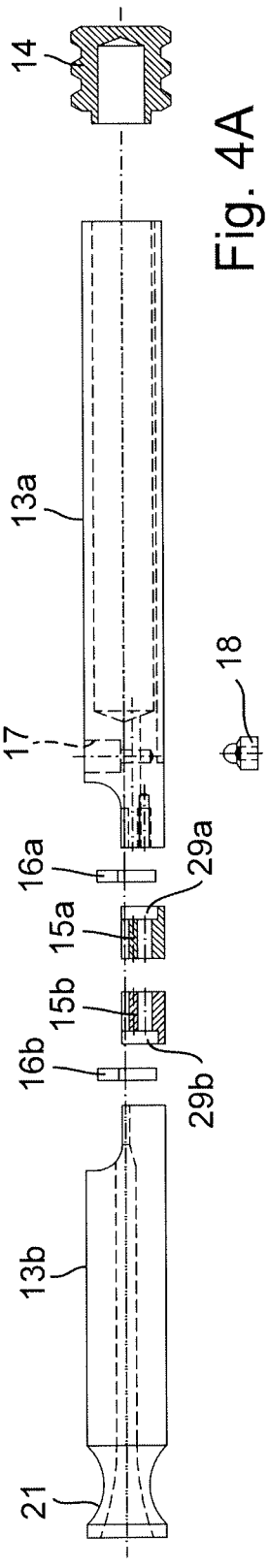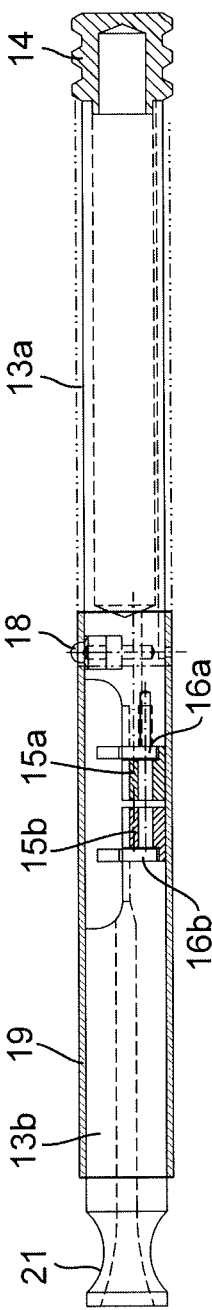

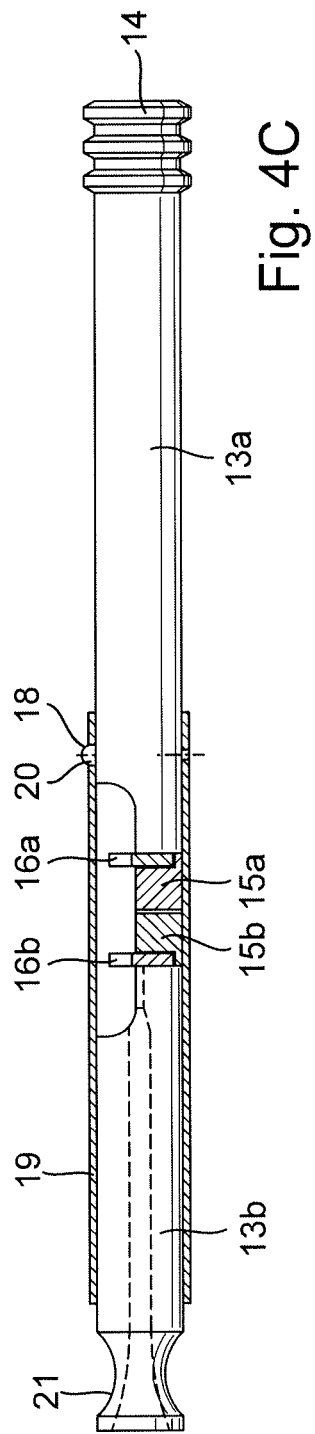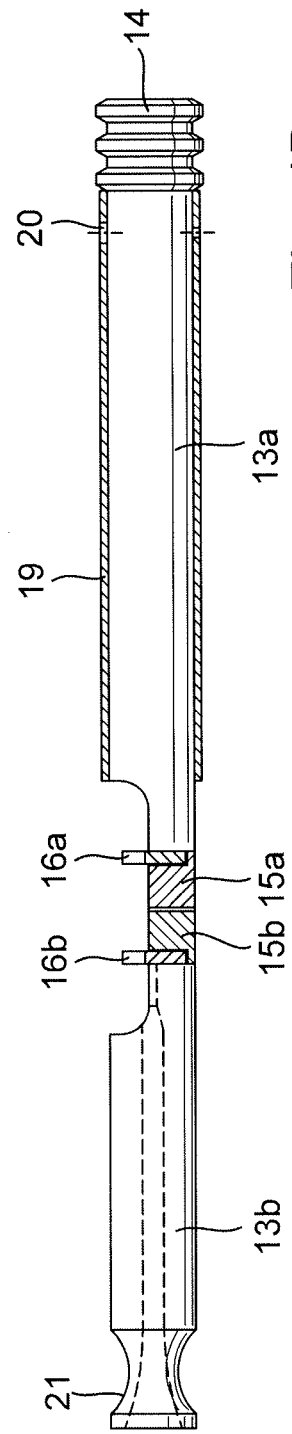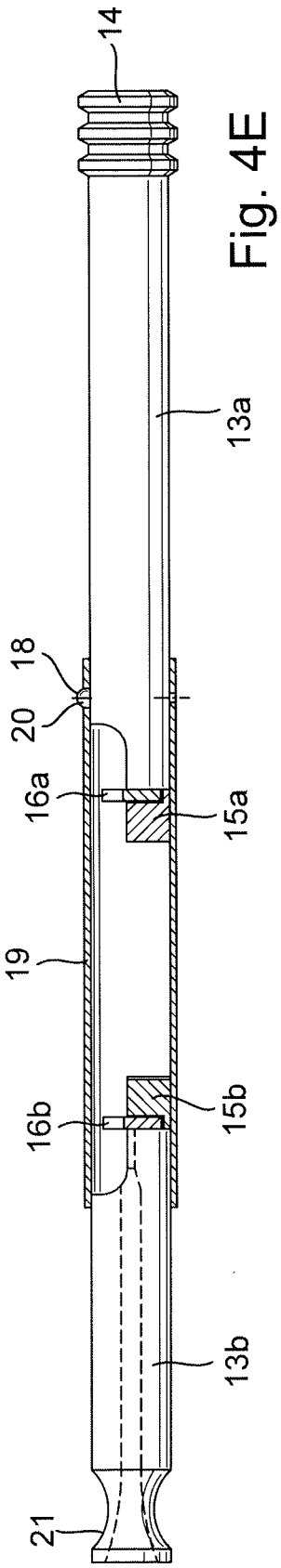

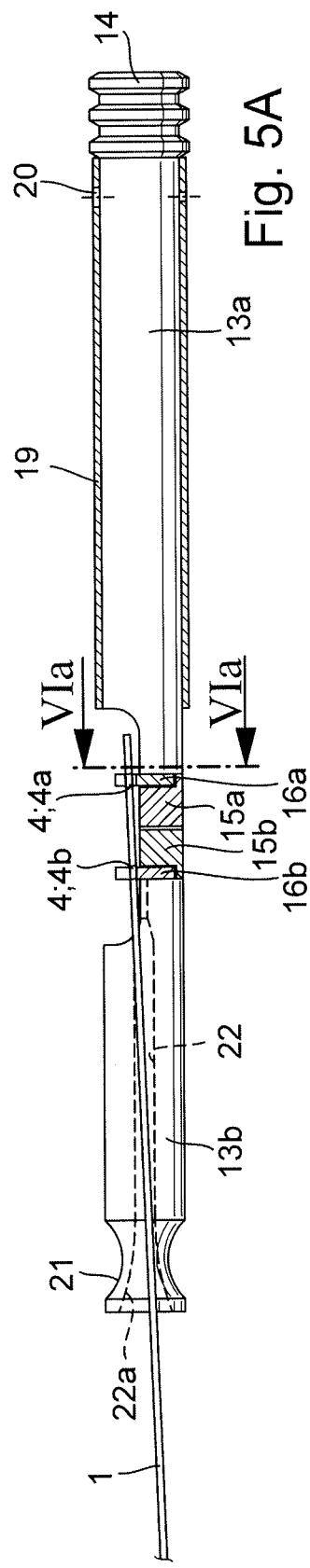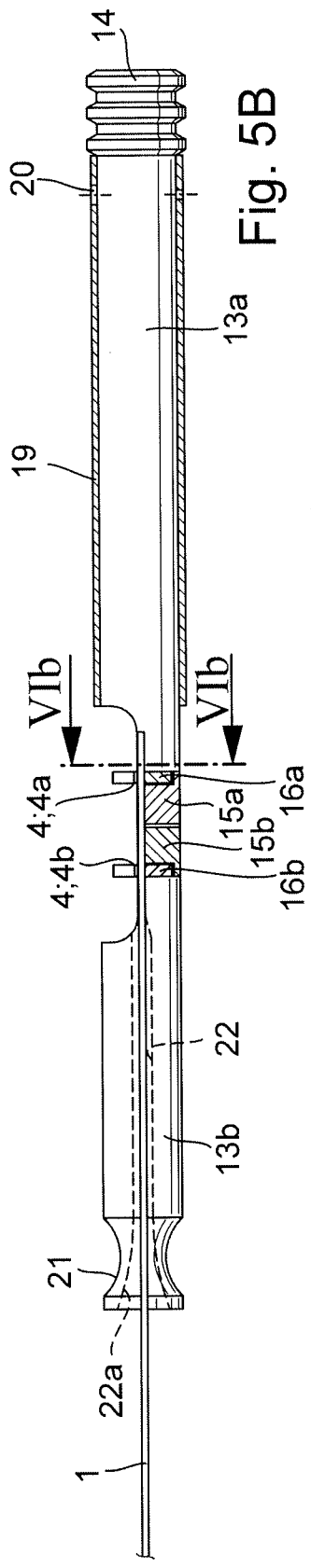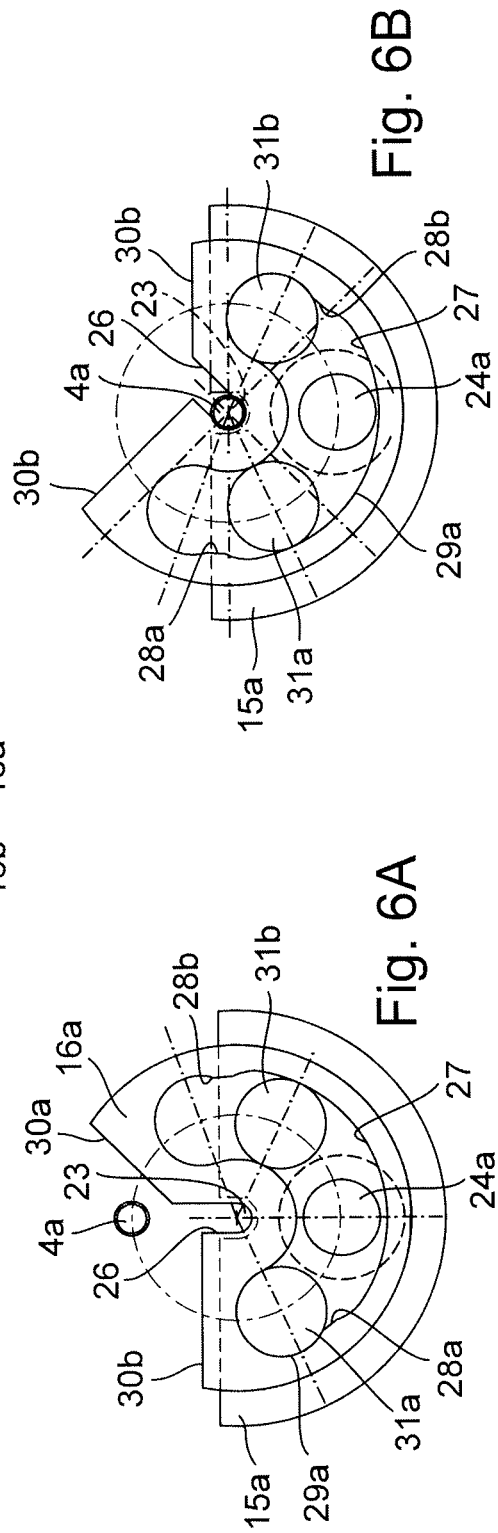

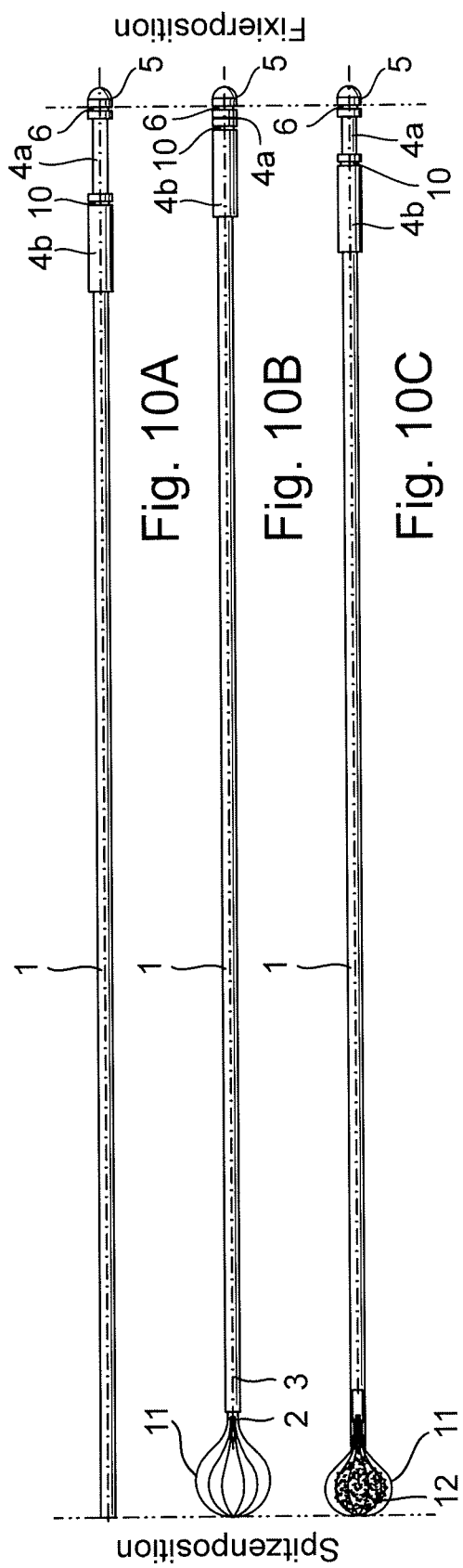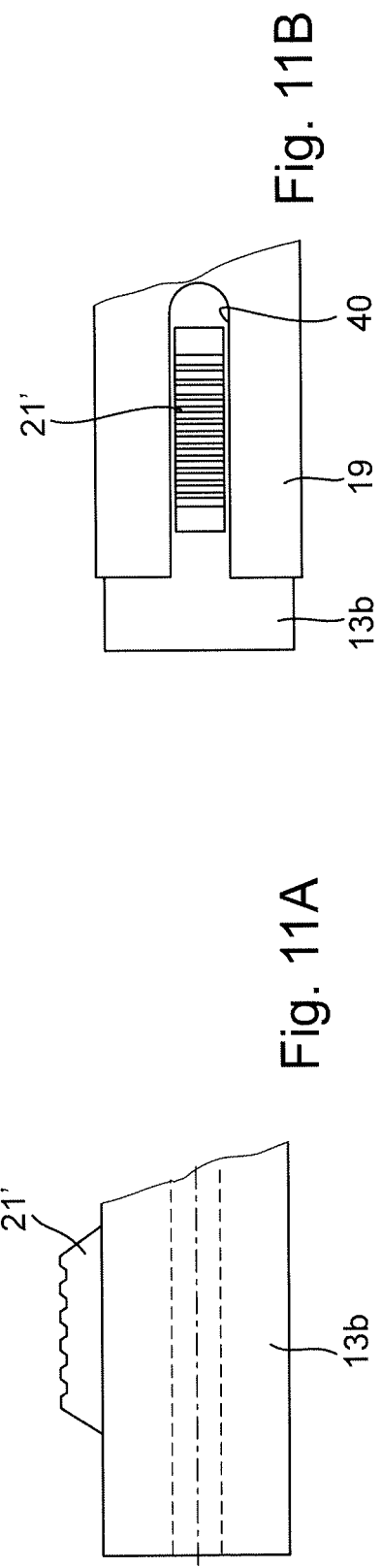

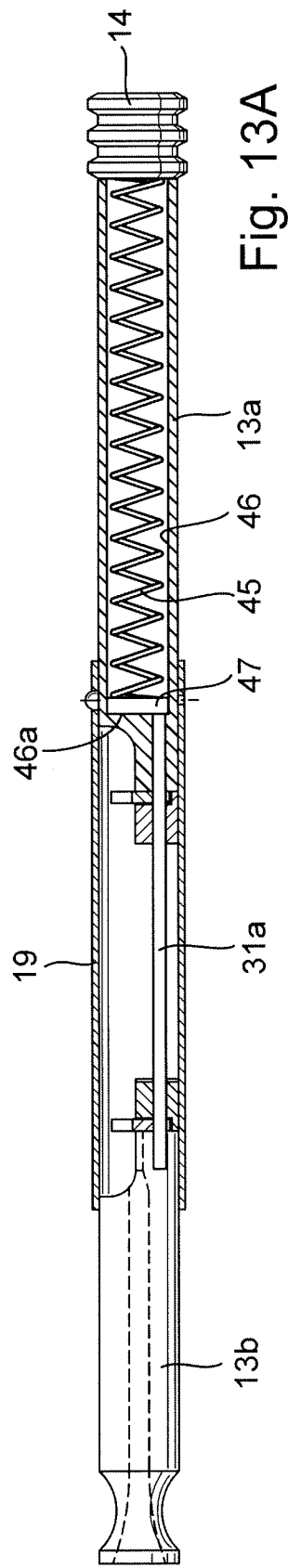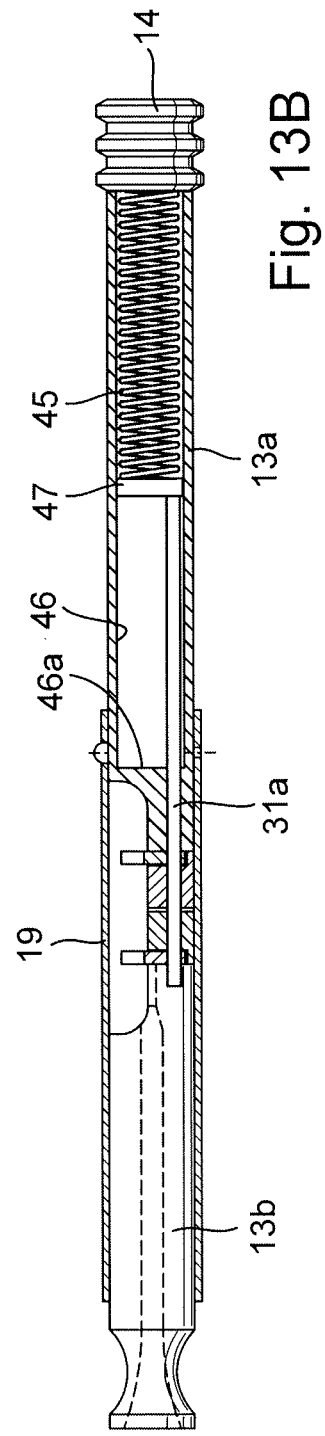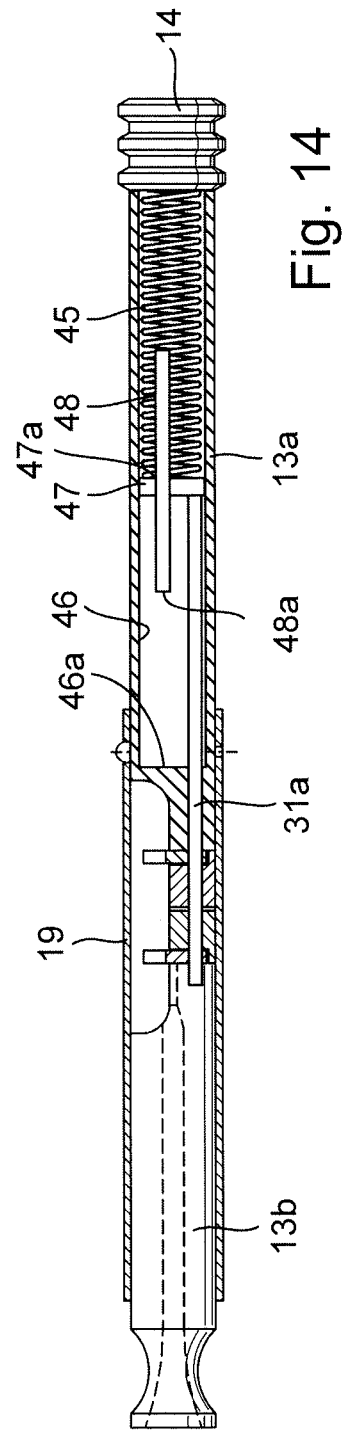

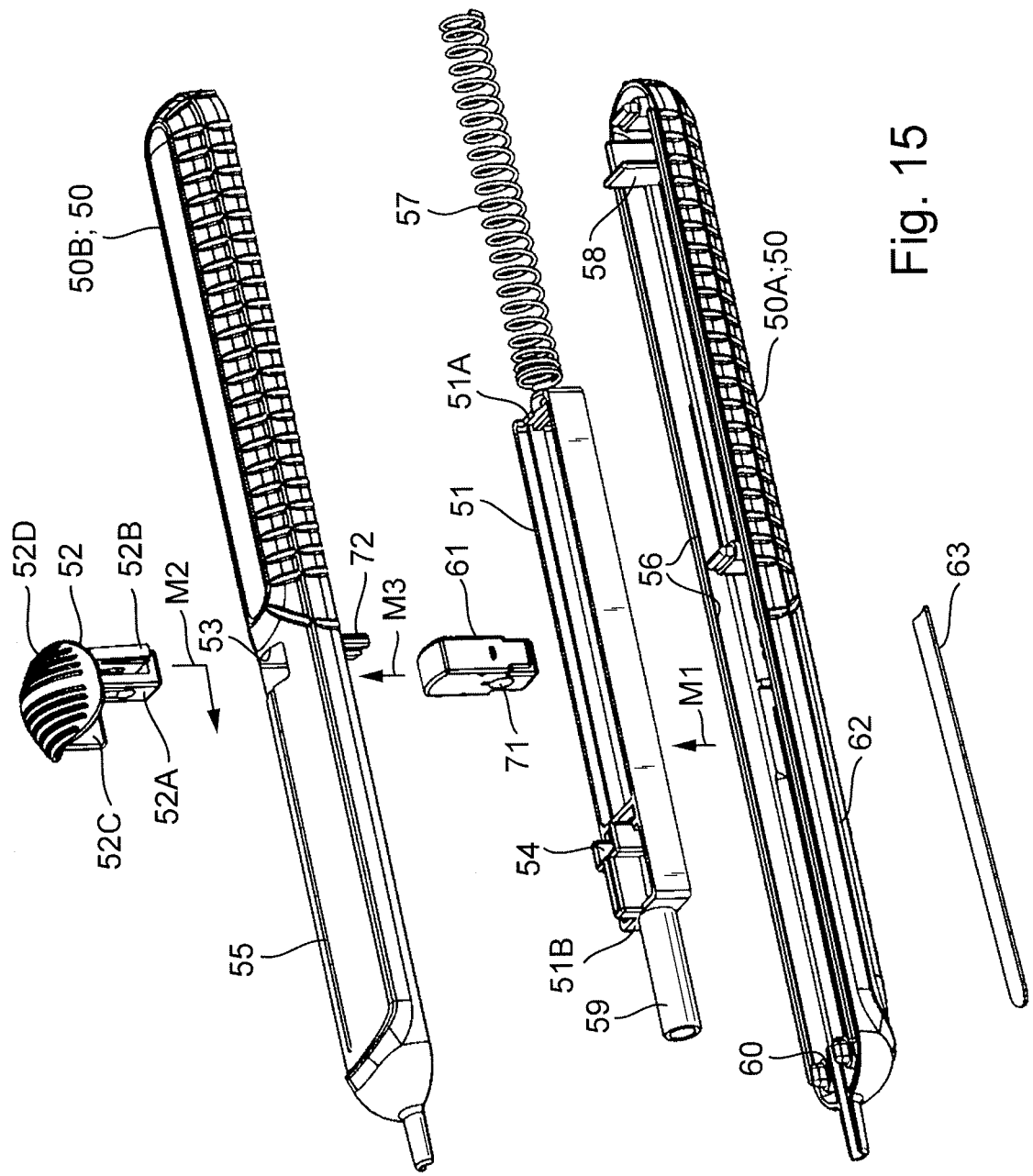

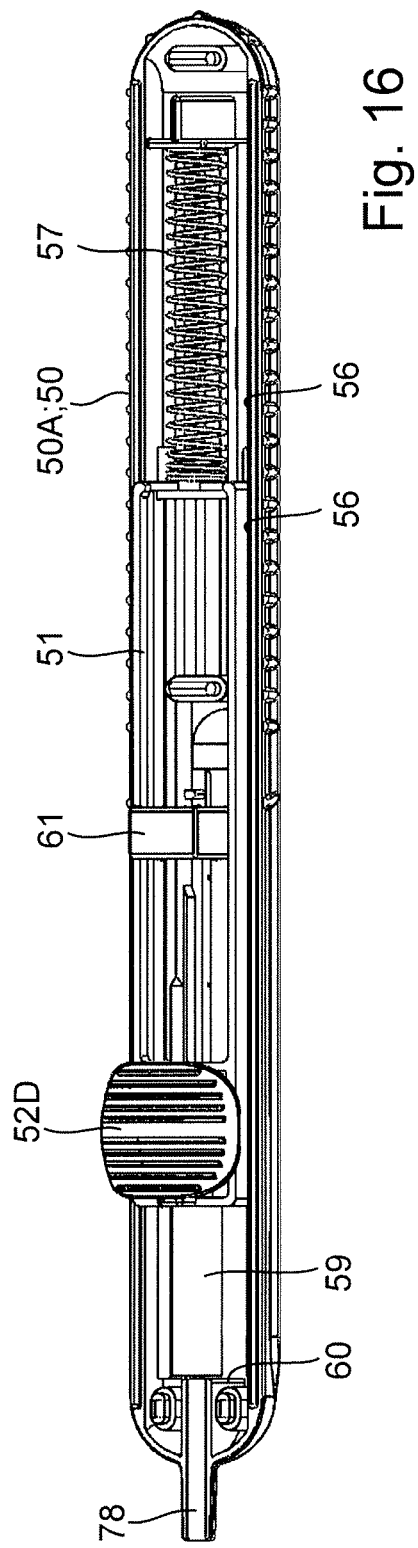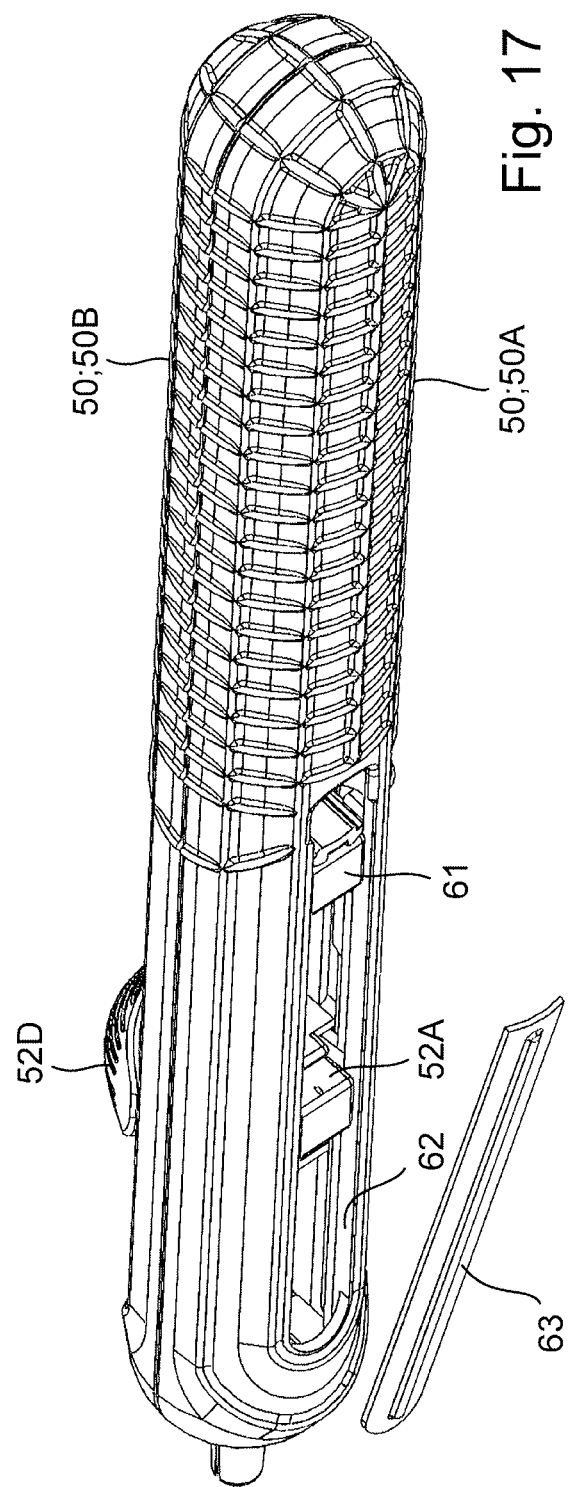

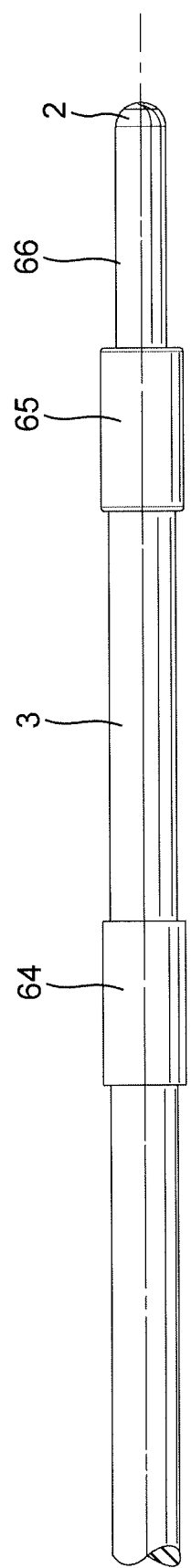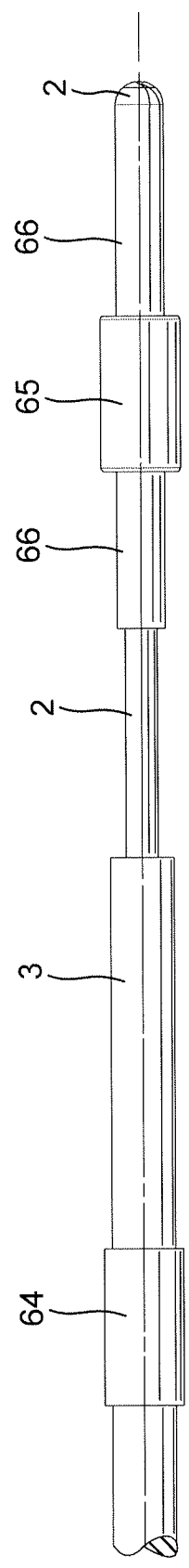

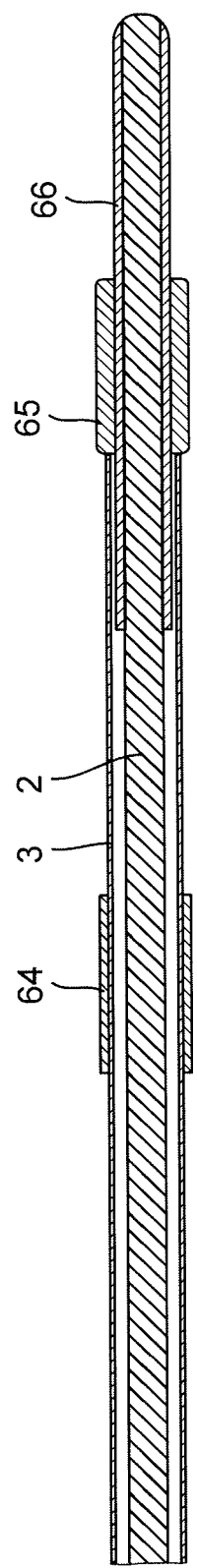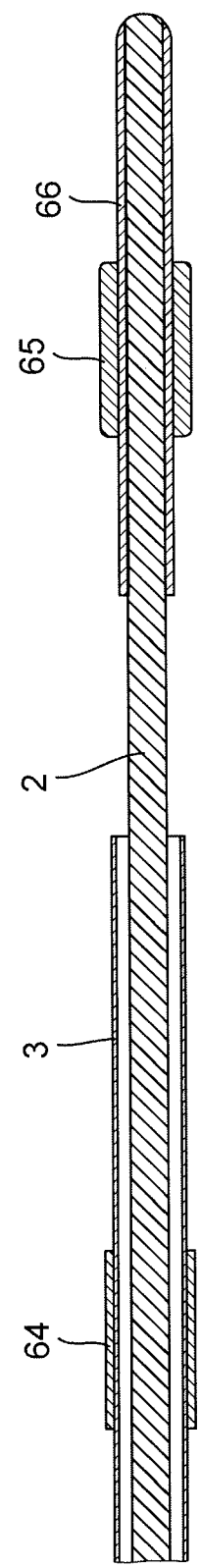

CHANGE-OUT HANDLE SYSTEM AND MEDICAL INSTRUMENT

CROSS-REFERENCE TO RELATED APPLICATIONS

This application is a continuation of PCT International Application No. PCT/EP2009/009256, filed Dec. 23, 2009, which claims priority under 35 U.S.C. §119 from German Patent Application No. DE 10 2009 022 379.7, filed May 22, 2009, the entire disclosures of which are herein expressly incorporated by reference.

BACKGROUND OF THE INVENTION

1. Field of the Invention

The invention relates to a change-out handle system for the releasable coupling of two elongated, axially relatively displaceable functional parts to a medical instrument unit that is couplable thereto and to a corresponding medical instrument.

2. Description of the Related Art

In the area of medical technology there are on occasions medical instruments which include two elongated, axially relatively displaceable functional parts, in particular for endoscopy applications. Important examples, among others, are stone catcher instruments with a wire basket that can be folded out to capture stones and the like in tissue cavities, wire filter instruments and guide wire units for catheter instruments. The two elongated, axially relatively displaceable functional parts can be, for example, a so-called wire pull and a tube, i.e. sheath, surrounding said wire pull.

The axial relative displacement of the two functional parts controls a distal functional element into at least two different functional states, in the case of a stone catcher instrument, for example, a distal wire basket is optionally controlled into a collapsed state retracted into the tube or into a folded-out state pushed forward out of the tube. At the proximal end, the two functional parts are typically coupled to a control handle in such a manner that the tube is connected to a stationary handle portion and the wire pull is connected to a handle portion that is to be actively manipulated. In the case of these types of conventional arrangements, once the instrument has been inserted into a body tissue canal, the tube consequently remains stationary with respect to said canal, whilst the wire pull is moved axially forward and backward by the proximal user manipulation in order, for example, to move a stone catcher basket distally out of the tube and to fold it open and after catching a stone, to move it back until it is secured. The wire basket consequently changes its axial position in the tissue canal during this functional movement, which can be undesirable or can make the stone catching function more difficult. Conventional handle systems for such applications also frequently have the problem that releasing the functional parts from the handle is often not possible or only possible with difficulty or is only possible when using loose connecting parts that may be lost and/or particular tools.

US disclosure document 2005/0113862 A1 discloses a handle system for releasably coupling two elongated, axially relatively displaceable functional parts of a medical instrument, in particular a guide wire unit, in the form of a central wire pull and a tube surrounding said wire pull, which has a deformable portion between its distal and its proximal end and between said deformable portion and the proximal end has a resiliently prestressing portion, through the prestressing force of which the axial length of the deformable portion can be modified. The wire pull and the tube are in each case fixedly connected to each other at the distal and at the proximal end. A handle with a front and a rear handle part can be used for manipulation, wherein the front handle part has an opening, through which the wire pull and the tube surrounding said wire pull are guided by way of a proximal end portion, which includes the resiliently prestressing portion. In this case, the proximal end portion of the wire pull and the tube are received loosely in an axial receiving bore of the rear handle part, and the tube portion connecting distally to the resiliently prestressing portion is releasably fixed on the front handle part by means of a screw clip. The two handle parts are guided together in an axially relatively displaceable manner for a predetermined length. Through the action of the resiliently prestressing portion, the deformable tube portion is held in a first form state. By manipulating the rear handle part, the deformable tube portion is moved out of said first into a second form state. In this case, the first form state serves to anchor the guide wire unit in a tissue canal in order, for example, to be able to push on and insert a catheter tube via the guide wire unit, whilst the second form state represents an insertion state, in which the guide wire unit can be moved into a tissue canal or out of said tissue canal again.

It is an object of the invention is to provide a change-out handle system of the aforementioned type, which enables a comparatively simple, functionally reliable, releasable coupling of the functional parts to the handle parts, an associated medical instrument unit and an associated medical instrument.

SUMMARY OF THE INVENTION

This and other objects are achieved in accordance with a first aspect of the invention by providing a change-out handle system comprising a first and a second handle part, which are arranged axially relatively displaceably one behind the other, wherein a first coupler is provided for the releasable, axially rigid coupling of a first of the two functional parts to the first handle part and a second coupler is provided for the releasable, axially rigid coupling of the second of the two functional parts to the second handle part. The second handle part has an opening for guiding through at least the first of the two functional parts. These structural measures create the prerequisite for a very simple, releasable coupling of the functional parts to the handle parts without further, e.g. loose parts or tools being forcibly needed for this purpose. The coupling both of the first functional part to the first handle part and of the second functional part to the second handle part being realized in an axially rigid manner ensures that each of the two functional parts can follow an axial movement of the associated handle part in a precise and practically play-free manner.

In a further development of the invention, the first and/or the second couplers have an associated manipulatable securing device, by way of which the respectively associated coupling connection of functional part and handle part is secured. This protects extensively against a possible unintended release of the relevant coupling connection.

In a further development of the invention, the first coupler has a first coupling element on the first handle part for the releasable coupling by way of a first counter coupling element to a rear end region of the first functional part. Consequently, the first functional part can be coupled by way of its rear end region releasably onto the first handle part by the two interacting elements.

In a further development of the invention, the second coupler has a second coupling element for the releasable coupling by way of a second counter coupling element to a rear end region of the second functional part. With these two elements, consequently, the second functional part can be coupled by way of its rear end region releasably onto the second handle part.

In a further development of the invention, the first and/or the second couplers have a respective groove or groove receiver and a corresponding groove receiver or groove in each case as a positive-locking coupling element/counter coupling element pair or a respective slot opening for forming a positive-locking pair with a respective retaining or bead element. The positive locking of said coupling ensures in an advantageous manner the releasable and axially rigid coupling of the respective functional part and handle part. In a further development of the invention, a manipulatable locking element is provided as a securing device for the respective coupling pair, by way of which securing device the connection is locked against release and unlocked for release. This secures the respective connection in an advantageous manner against unintended release.

In a further development of the invention, there is provided a variable stroke limiting element by way of which the relative axial stroke displacement path between the first and second handle part can be adjusted in a variable manner. This is useful, for example, in the case of stone catcher instruments when the handle parts are used for instruments with different wire basket lengths.

In a further development of the invention, there is provided a resilient prestressing element which acts in the axial direction between the two handle parts. This means that the two handle parts can be held, prestressed, in one of their two end positions, out of which they can then be relatively displaced by the user actively in the direction of the other end position.

In a further development of the invention, the second handle part forms a handle part which is to be actively manipulated and which is actively manipulated by the user in order to carry out the intended useful function of the two functional parts.

In a further development of the invention, the first handle part forms a rear handle part and the second handle part forms a front handle part. In this case, for example, the front handle part can represent the handle part which is to be actively manipulated. Consequently, in this case, the functional movement includes active displacement of the front handle part and of the second functional part coupled thereto, whilst the rear handle part and the first functional part coupled thereto can remain stationary, i.e. do not need to experience any noticeable axial change in position.

In a further development of this aspect of the invention, the opening widens outwards in the shape of a funnel in a front end region of the front handle part. This makes it easier to insert at least the first of the two functional parts for the purposes of coupling with the rear handle part.

In a further development of the invention, there is provided a handle cover tube which is guided in an axially displaceable manner on the rear handle part and releases a front end portion of the rear handle part and a rear end portion of the front handle part in an axially rear end position and covers them in an axially front end position. This measure offers advantages, on the one hand, when coupling the functional parts to the handle parts, for which purpose the handle cover tube is preferably in its axial rear end position, and, on the other hand, during the useful operation of the two functional parts, for which purpose the handle cover tube is preferably moved into its axially front end position. In a further development of this measure, there is provided a latch by way of which the handle cover tube can be latched releasably in its axially front end position. This favors secure handle control when the functional parts are in use.

In another advantageous further development of the invention, the first handle part is developed as a handle body with a carriage guide, and the second handle part forms a slider element which is to be actively manipulated and is guided on the handle body in an axially displaceable manner by the carriage guide. Consequently, in this case, the functional displacement to carry out the intended useful function of the two couplable functional parts includes active displacement of the slider element and consequently of the functional part coupled thereto, whilst the handle body and the functional part coupled thereto can remain substantially stationary.

In a development of this aspect of the invention, the slider element includes a carriage body and a control head body, which is retained thereon so as to be transversely displaceable and forms the associated securing device for securing the coupling connection between the handle control part and the second functional part, wherein it is transversely displaceable between a latching slide control position and a position disengaging the securing function. In this way, the control head body fulfills both a control element function in normal use and a coupling function for releasably retaining the associated functional part.

According to another aspect the invention provides a medical instrument unit which is developed in a particular way in such a manner that it can be coupled in a comparatively simple, reliable and functionally secure manner to a change-out handle system which, in particular, can be a change-out handle system according to the invention. To this end, two elongated functional parts, which form a substantial part of the instrument unit, are provided with suitable counter coupling elements. More specifically, the medical instrument unit comprises a first elongated functional part with a first counter coupling element provided on a rear end region for the releasable, axial rigid coupling to a first handle part of a change-out handle system and a second elongated functional part, which is axially relatively displaceable with respect to the first functional part with a second counter coupling element provided on a rear end region for the releasable axially rigid coupling to a second handle part of the change-out handle system.

In a further development of the invention, the first counter coupling element is formed by a first connection piece provided on the first functional part and the second counter coupling element is formed by a second connection piece provided on the second functional part, wherein a resilient element acts in the axial direction between the two connection pieces. This can be used, in particular, through the action of the resilient element, to prestress the two functional parts into a predeterminable axial relative position, out of which they can be displaced axially towards each other by active user manipulation.

In a further development of this aspect of the invention, the two functional parts are formed by a wire pull and a tube surrounding said wire pull, e.g. a medical endoscopy instrument. In a further development of the invention, in this case the wire pull represents the first functional part and the tube represents the second functional part. In a realization in which the front handle part or the slider element forms the handle part which is to be actively manipulated, the result is that the tube forms the actively manipulated functional part, whilst the wire pull forms the functional part that remains stationary with respect to it. This has the advantage, which is very desirable in many cases, that the wire pull and a distal functional element provided thereon, where applicable, remains substantially fixed axially during the functional manipulation, e.g. in its position inserted into a tissue canal, and essentially only the tube is displaced axially in relation to the tissue canal.

In a further development of this aspect of the invention, the medical instrument unit is a stone catcher instrument. For this, the aforementioned design variants with an actively manipulated front handle part or an actively manipulated slider element have the advantage that the axial position of the stone catcher basket in the tissue canal can be held in an extensively constant manner during the folding-out movement and the drawing-together movement. This makes it considerably easier to catch and retain a stone or the like in a functionally secure and reliable manner.

In yet another development of this aspect of the invention, the change-out handle system includes an entry-aiding sleeve, which surrounds the tube and is attached releasably on the front handle part in a rest position and is displaceable out of the rest position forwards as far as the distal end region of the wire pull and tube into an entry-aiding position. In the entry-aiding position, the entry-aiding sleeve makes it easier to insert the distal end region of the wire pull and tube and, in the case of a stone catcher instrument, it also protects the susceptible stone catcher basket.

According to yet another aspect the invention provides a medical instrument including a change-out handle system according to the invention in combination with a medical instrument unit according to the invention. In a further development of the invention, this is an endoscopy instrument, wherein the medical instrument unit is couplable to an endoscopy handle body by means of a telescopic adapter sleeve. By way of said adapter sleeve, the length of which can be modified telescopically, the medical instrument unit, in its in-use state coupled to the change-out handle system, can be coupled in a very convenient manner to the endoscopy part.

Other objects, advantages and novel features of the present invention will become apparent from the following detailed description of one or more preferred embodiments when considered in conjunction with the accompanying drawings.

BRIEF DESCRIPTION OF THE DRAWINGS

FIG. 1A shows a side view of a medical stone catcher instrument, with the basket in the retracted state;

FIG. 1B shows a side view of a proximal connection end portion of the stone catcher instrument in FIG. 1A;

FIG. 1C shows a longitudinal sectional view of the connection end portion in FIG. 1B;

FIGS. 2A to 2C show views corresponding to FIGS. 1A to 1C, in the state with the stone catcher basket fully folded out;

FIGS. 3A to 3C show views corresponding to FIGS. 1A to 1C in a state with a stone caught and secured;

FIG. 4A shows an exploded longitudinal sectional view of a change-out handle system with a handle unit for the stone catcher instrument in FIGS. 1A to 3C;

FIGS. 4B and 4C show a longitudinal sectional view or side view of the handle unit in the assembled state with a handle cover tube in a front end position;

FIG. 4D shows a side view corresponding to FIG. 4C, but with the handle cover tube in a rear end position;

FIG. 4E shows a side view corresponding to FIG. 4C, but in a state with the handle parts extended apart;

FIG. 5A shows a side view corresponding to FIG. 4D with the stone catcher instrument added before a final coupling;

FIG. 5B shows a side view corresponding to FIG. 5A with the stone catcher instrument coupled to the handle unit in readiness;

FIGS. 6A and 6B show cross-sectional views along the line VIa-VIa in FIG. 5A or along the line VIb-VIb in FIG. 5B;

FIGS. 10A to 10C show side views, comparing positions of the stone catcher instrument without the handle unit in the state with the catcher basket retracted, the catcher basket moved out or in the state with a stone caught and secured;

FIGS. 11A and 11B show a side view or a top view of the front end region of the front handle part for a variant with a slider element as the control manipulating means instead of a recessed handle;

FIGS. 13A and 13B show side views corresponding to FIG. 4E or 4C for a handle variant with a resilient prestressing element for the two handle parts, in the extended or pressed-together handle end position;

FIG. 14 shows a view corresponding to FIG. 13B for a handle variant with a variable stroke limiting means;

FIG. 15 shows an exploded view of a further change-out handle system suitable, for example, for medical stone catcher instruments;

FIG. 16 shows a side view of the change-out handle system in FIG. 15 in the assembled state with the top shell removed;

FIG. 17 shows a side view inclinedly from below of the assembled change-out handle system in FIG. 16;

FIGS. 19A and 19B show side views of an end region, developed for coupling to the change-out handle system in FIG. 15, of a medical instrument unit, with its two elongated functional parts in a state fully pushed together or in a state moved apart somewhat;

FIGS. 19C and 19D show a respective longitudinal sectional view of the views in FIG. 19A or 19B;

DETAILED DESCRIPTION OF THE PREFERRED EMBODIMENTS

Figure 7:
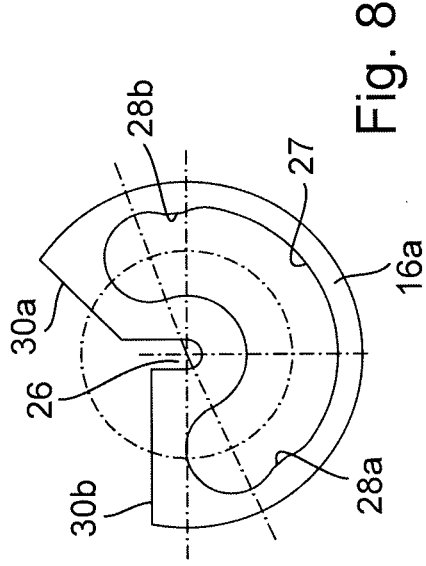
FIG. 7 shows a top view of a coupling element part of a coupling connection illustrated in FIGS. 6A and 6B.

The invention is illustrated in an exemplary manner in the figures in applications of change-out handle systems for medical stone catcher instruments, the expert readily recognizes from this, however, that the change-out handle system is suitable in an identical manner for any other applications and in particular for medical instruments where two elongated, axially relatively displaceable functional parts are to be coupled releasably to a handle system, typically for the purpose of operating the functional parts via the handle system.

FIGS. 1A to 1C show a stone catcher instrument 1 which includes, as usual, an elongated, central wire 2, usually called a wire pull, and a sheathing 3 surrounding said wire pull, in the present case also referred to as a tube. At the proximal end of the stone catcher instrument 1 there is provided a connection unit 4, which comprises a first connection piece 4a and a second connection piece 4b which is axially relatively displaceable in relation to said first connection piece. The first connection piece 4a has a hollow cylindrical shape with a head part 5, which locks proximally with a hemisphere 5a, to which an annular groove portion 5b with an attached annular groove 6 connects distally. The wire pull 2 extends with its proximal end region through the hollow cylindrical bore of the first connection piece 4a as far as to its head part 5, to which it is fixedly connected in a suitable conventional manner, e.g. by laser welding or bonding.

At the front end, the first connection piece 4a is provided with a piston 7, with which it is guided in an axially displaceable manner in a cylinder chamber 8 of the second connection piece 4b. In other words, the two connection pieces 4a, 4b are axially displaceable in relation to each other in the manner of a piston/cylinder unit. A helical spring 9, inserted into the cylinder chamber 8, prestresses the two connection pieces 4a, 4b into their extended end position shown in FIGS. 1A to 1C. The wire pull 2 extends longitudinally centrally through the second connection piece 4b, wherein this latter has corresponding end-face through-bores from the cylinder chamber 8 to the outside. The tube 3 is fixedly connected to the second connection piece 4b, in particular to its front end face region, e.g. by means of a usual adhesive connection or another connection means usual for this purpose. An annular groove 10 is provided in the cylindrical outer casing of the second connection piece 4b.

FIGS. 2A to 2C show the stone catcher instrument in a state in which a wire basket or stone catcher basket 11, provided at the distal end of the wire pull 2, is completely released from the tube 3 and consequently is situated in a fully unfolded state. In this state, the two connection pieces 4a, 4b are situated in their other end position, pressed together in opposition to the force of the helical spring 9, in which position the first connection piece 4a is inserted in a maximum manner into the second connection piece 4b.

If, proceeding from the state in FIGS. 2A to 2C, the operating force, which is to be applied by a user and presses the two connection pieces 4a, 4b together in opposition to the force of the helical spring 9, is released again, the helical spring 9 presses the two connection pieces 4a, 4b apart again as far as the opposing end position as shown in FIGS. 1A to 1C in which the wire basket 11, completely collapsed, is removed from the distal end portion of the tube 3.

When, with the stone catcher instrument 1 in use, a stone 12, as illustrated in FIGS. 3A to 3C, is caught by the wire basket 11 and the user then releases the retraction of the wire basket 11, the wire basket 11 collapses under the effect of the helical spring 9 until it secures the stone 12 in a clamping manner. This represents the state of the stone catcher instrument 1 illustrated in FIGS. 3A to 3C.

FIGS. 4A to 4E show a change-out handle system with a handle unit, with which the stone catcher instrument 1 in FIGS. 1 to 3C can be coupled releasably by means of its connection unit 4 so that a user can carry out the abovementioned usual functional movements of the stone catcher instrument 1 by operating the handle unit, i.e. the handle unit in combination with the connection unit 4 forms a change-out handle system for the stone catcher instrument 1.

As the exploded representation in FIG. 4A shows, the handle unit comprises a first rear handle part 13a, a second front handle part 13b, a proximal termination stopper 14, a first groove receiving piece 15a, a second groove receiving piece 15b, a first locking element 16a, a second locking element 16b and a latching pin 18 to be inserted into a pin receiver 17 in the rear handle part 13a for latching a handle cover tube 19 shown in FIG. 4B in a latched front end position. FIGS. 4B and 4C show the handle unit in the assembled state. To this end, the first groove receiving piece 15a is secured at the distal end face of the rear handle part 13a, e.g. by means of a screw-type connection, and the second groove receiving piece 15b is fixed at the proximal end face of the front handle part 13b, e.g. also by means of a screw-type connection. The first securing or locking element 16a, in this case, is held so as to be pivotable in a receiver 29a of the first groove receiving piece 15a between the latter and the rear handle part 13a, and in an analogous manner, the second securing/locking element 16b is held so as to be pivotable in a receiver 29b of the second groove receiving piece 15b between the latter and the front handle part 13b.

FIGS. 4C and 4D show a side view of the handle unit, wherein merely the handle cover tube 19 is shown in a sectioned manner so that the inner components are easier to see. As illustrated in FIGS. 4C and 4D, the handle cover tube 19 is held on the rear handle part 13a so as to be axially displaceable, wherein it is locked releasably in its front end position in FIG. 4C by engagement of the elastically flexible latching pin or pushbutton 18 into a corresponding latching opening 20. In this position, the handle cover tube 19 covers a front end region of the rear handle part 13a and a rear end region of the front handle part 13b including the groove receiving pieces 15a, 15b and the locking elements 16a, 16b. In a front portion, which is not covered by the handle cover tube 19 in its front end position, the front handle part 13b is provided with a handle recess 21 which runs round the periphery. By pressing in the latching pin 18 radially, the latching of the handle cover tube 19 can be released and this latter can then be pushed back until it is as far back as possible in the rear end position in FIG. 4D. In this position, it releases the front handle part 13b and a front end region of the rear handle part 13a including the groove receiving pieces 15a, 15b and locking elements 16a, 16b.

As shown in FIG. 4E, the two handle parts 13a, 13b are arranged so as to be axially relatively displaceable, i.e. proceeding from the position in FIGS. 4B to 4D where they are pushed together as far as possible, they can be pushed apart axially. In this case, they are guided by means of guide bars (not shown in any more detail) which extend longitudinally right through axial bores which are provided in the groove receiving pieces 15a, 15b and/or the handle parts 13a, 13b themselves. In addition, the front handle part 13b is also guided on the side of the periphery through the handle cover tube 19 when said tube is situated in its latched front end position, see FIGS. 4C and 4E.

FIGS. 5A and 5B illustrate the coupling of the stone catcher instrument shown in FIGS. 1A to 3C to the handle unit shown in FIGS. 4A to 4E. As illustrated in FIG. 5A, to this end the stone catcher instrument 1 with its proximal connection unit 4 in front is pushed from front to back through an opening 22, which is provided as a central longitudinal bore right through the front handle part 13b. To make inserting the stone catcher instrument 1 easier, the opening 22 has a widening 22a which opens towards the front in the shape of a funnel. In exemplary dimensioning, the outside diameter of the stone catcher instrument 1 is in the order of magnitude of approximately 1 millimeter, whilst the opening 22 has a suitably larger diameter. The stone catcher instrument 1 is pushed into the handle unit until the annular groove 6 provided on the first proximal connection piece 4a is situated at the level of the rear locking element 16a. The distance between the two locking elements 16a, 16b in the coupling position shown in FIG. 5a, in which the two handle parts 13a, 13b are pushed together as far as is possible, is selected such that it is identical to the distance between the two annular grooves 6, 10 of the connection unit 4 in their prestressed end position as shown in FIGS. 1A to 1C, which, at the same time, is the coupling assembly position of the stone catcher instrument 1. The result of this is that the annular groove 10 provided on the front connection piece 4b is situated at the level of the locking element 16b arranged on the front handle part 13b.

Once this axial position of the stone catcher instrument 1 as shown in FIG. 5A has been obtained, with its connection unit 4 at the level of the region of the groove receiving pieces 15a, 15b of the handle unit, the stone catcher instrument 1 can be coupled to the handle unit by, with slight pressure from above, shown in FIG. 5A, the connection unit 4 with its annular grooves 6, 10 being moved into coupling, axially rigid operative connection with the groove receiving pieces 15a, 15b and securing elements 16a, 16b and thereby with the respective handle part 13a, 13b. This means that the stone catcher instrument 1 passes from a slightly inclined insertion position as shown in FIG. 5A into its precisely axial in-use position as shown in FIG. 5B. The coupling of the rear connection piece 4a to the groove receiving piece 15a of the rear handle part 13a, effected in this manner, is then locked against unintended release by the locking element 16a, and the coupling of the front connection piece 4b to the groove receiving piece 15b of the front handle part 13b also being secured against unintended release by the locking element 16b. In this way, the wire pull 2 of the stone catcher instrument 1 is coupled in an axially rigid manner via the rear connection piece 4a and in a releasable manner with the rear handle part 13a, and the tube 3 of the stone catcher instrument 1 is coupled in an axially rigid manner with the front handle part 13b via the front connection piece 4b of the connection unit 4.

Figure 8:
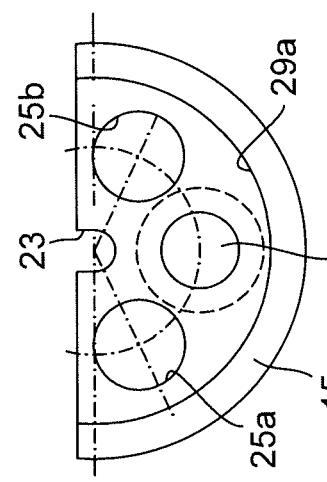
FIG. 8 shows a top view of a securing element for the coupling connection illustrated in FIGS. 6A and 6B.

FIGS. 6A and 6B, in conjunction with the individual representations in FIG. 7 and FIG. 8, show the lockable coupling in a more precise manner by way of the example of the coupling connection between the rear connection piece 4a on the rear handle part 13a of the groove receiving piece 15a and the locking element 16a. As can be seen from FIG. 7, the groove receiving piece 15a (and the other groove receiving piece 15b in an identical manner) has an approximately semi-cylindrical shape with a central, axial receiving slot 23, in which the stone catcher instrument 1 with its corresponding portion of the connection unit 4 can be received. An axial screw opening 24 is used for guiding through a stud 24a, by way of which the groove receiving piece 15a is fastened on the relevant end face of the associated handle part 13a. In addition, two axial openings 25a, 25b are provided in the groove receiving piece 15a, through each of which openings a guide bar 31a, 31b is guided in order to guide the two handle parts 13a, 13b together in an axially displaceable manner, as mentioned above.

As can be seen from FIG. 8, the locking element 16a (and the other locking element 16b in an identical manner) is formed as a disk-shaped element with an open disk element which extends over somewhat less than 270° with a central axial receiving slot 26, which functions as a groove receiver for the corresponding annular groove 6, to be received, of the connection piece 4a, to be coupled, of the stone catcher instrument 1. This means that the width of the receiving slot 26 is selected such that it corresponds approximately to the outside diameter of the connection piece 4a in the region of the annular groove 6 or is only slightly larger, but is smaller than the outside diameter of the connection piece 4a in the region of the head part portion 5b outside the annular groove 6. In addition, the axial length of the locking element 16a corresponds to that of the annular groove 6 or is at most slightly smaller. In addition, the locking element 16a is provided with a half-ring-shaped guide slot 27, the width of which corresponds approximately to the diameter of the guide bar openings 25a, 25b of the groove receiving piece 15a and the corresponding diameter of the guide bars 31a, 31b passed through, as a result of which the locking element 16a is guided, at a measurement determined by the angular extension of the guide slot 27, in a pivotable manner in the corresponding receiver 19a by means of the guide bars 31a, 31b. The guide slot 27 is provided with a narrow point 28a, 28b at each of the two end regions, as a result of which the locking element 16a is latched in each of its two end positions, as shown in FIGS. 6A and 6B, at each one of the two guide bars 31a, 31b.

In the assembly position in FIG. 6A, the connection piece receiving slot 23 of the groove receiving piece 15a and the groove receiving slot 26 of the locking element 16a are both aligned open upwards. Through the pressing-in movement depicted above, the connection piece 4a, lying beforehand over the two slots 23, 26 as shown in FIGS. 5A and 6A, moves into its central position in the slots 23, 26, wherein the annular groove 6 passes into the groove receiving slot 26 and this means that the connection piece 4a and consequently the wire pull 2 fixed thereto is coupled in an axially rigid manner with the associated handle part 13a. By pivoting the locking element 16a from its assembly/unlocking position as shown in FIG. 6A, the depicted coupling connection is secured against release by the groove receiving slot 26 being rotated in relation to the connection piece-receiving slot 23, which remains stationary, and the common overlapping opening width of both slots 23, 26 being thereby reduced to a value smaller than the diameter of the annular groove 6. Consequently, the wire pull 2 of the stone catcher instrument 1 is held on the rear handle part 13a locked by its associated connection piece 4a. To release the coupling connection, the locking element 16a is pivoted from its locking position as shown in FIG. 6B back into its unlocking position as shown in FIG. 6A. The control of the locking element 16a for locking and unlocking is made easier by the open disk shape, the two end surfaces 30a, 30b of which form respective control surfaces, the user pressing on said surfaces to effect the locking or unlocking pivoting movement of the locking element 16a.

It is obvious that in the identical manner the releasable coupling of the tube 3 of the stone catcher instrument 1 to the front handle part 13b is effected via the front connection piece 4b and the associated coupler, i.e. via the groove receiving piece 15b and the locking element 16b arranged in a pivotable manner in the receiver 19b of said groove receiving piece 15b. This includes, in particular, the inserting of the front connection piece 4b into the associated receiving slot of the groove receiving piece 15b and, at the same time, of its annular groove 10 into the groove receiving slot of the locking element 16b simultaneously with the above-described inserting of the rear connection piece 4a into the corresponding slots 23, 26 of the groove receiving piece 15a or of the locking element 16a and the subsequent locking of said coupling connection by correspondingly rotating the locking element 16b. Thus, the stone catcher instrument 1 with the wire pull 2 and the tube 3 assumes its in-use position shown in FIG. 5B, in which the wire pull 2 is coupled with the rear handle part 13a in a releasably locked manner so as to be axially rigid and the tube 3 is coupled in the same way with the front handle part 13b in a releasably locked manner so as to be axially rigid.

It is obvious that as an alternative to the coupler/securing device shown in FIGS. 6A to 8, arbitrary other conventional coupler/securing devices are usable, as can be realized by the expert in a conventional manner by using force-fitting and/or positive-locking connections to fulfill the depicted coupling and securing functionalities. Thus, the arrangement of groove, on the one hand, and groove receiver or groove engagement element, on the other hand, on the relevant connection piece or on the relevant handle part can be exchanged against the variants described above. For securing or locking the releasable groove-groove engagement element connection, instead of the above explained rotational movement of the respective locking element 16a, 16b, other securing movements with correspondingly modified locking elements can be used, e.g. the arranging of a slot-covering locking element, which can be moved rotationally about a transverse axis perpendicular to the longitudinal axis of the handle part in order, as an option, to cover or release the receiving groove with the received groove engagement element. Further solution variants are a blocking element which is pivotable between a groove covering position and a release position about a tilt axis, which is parallel to the longitudinal axis of the handle part but is offset, a blocking element which is movable in a similar manner so as to tilt about a transverse axis which is perpendicular to the longitudinal axis of the handle part, or a blocking slider element which is displaceable in a translatory manner between a blocking position and a release position.

Arbitrary conventional means can be used, such as joint hinges, film hinges or plug-in axles, for the rotationally displaceable fixing. The fixing of the respective locking element in its locking position can be realized, for example, by the handle cover tube 19. This prevents unintended unlocking without further fixing aids. For example, this fixing of the locking can be developed such that the locking element is freely displaceable in the rear position of the handle cover tube 19 between its blocking position and its release position, whilst, when the handle cover tube 19 has been pushed forward, it is no longer displaceable out of its blocking position into the release position.

Figure 9A:
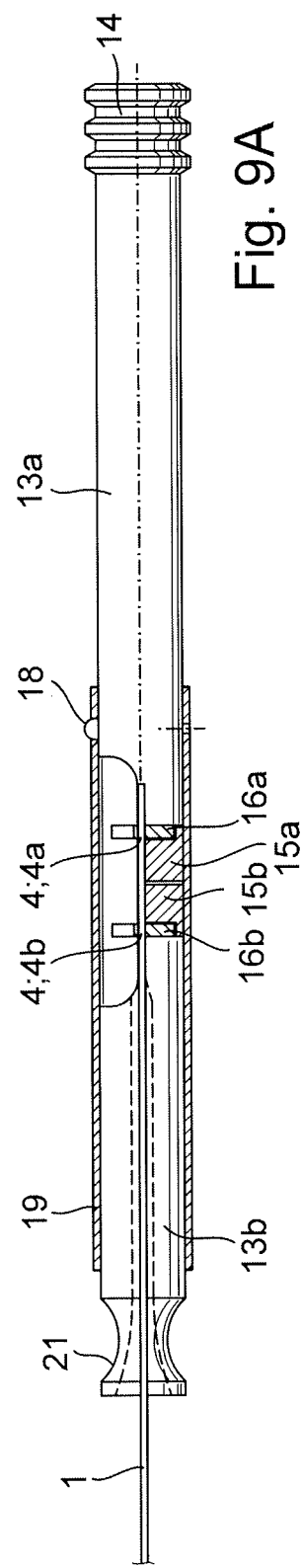
FIGS. 9A and 9B show in each case a side view corresponding to FIG. 5B in the operating state with the stone catcher basket extended or retracted.
Figure 9B:
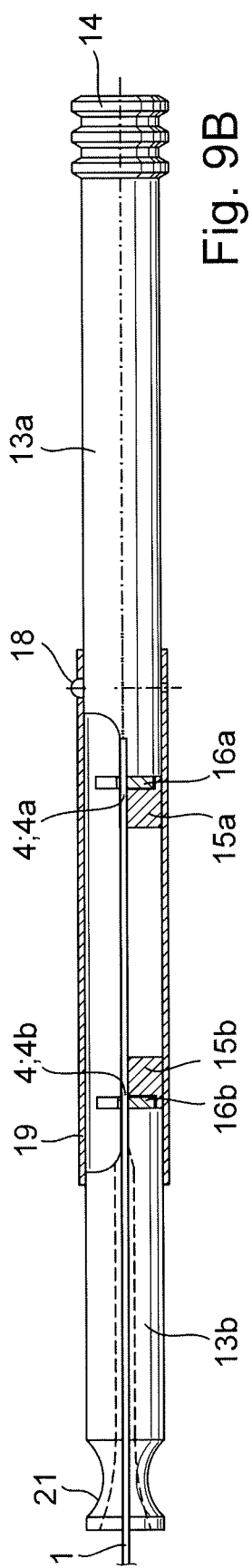

FIGS. 9A and 9B show the operation and method of functioning of the stone catcher instrument 1 coupled with the handle unit in this manner in readiness for use. In the handle position in FIG. 9A with the two handle parts 13a, 13b pushed together as far as is possible, the two connection pieces 4a, 4b of the connection unit 4 are correspondingly situated in their maximum pushed-together or pressed-together position as shown in FIGS. 2B and 2C, i.e. the stone catcher instrument 1 is situated in its state with the stone catcher basket 11 completely extended as in FIG. 2A. In the functional state in FIG. 9B, with the handle parts 13a, 13b pushed apart to the maximum, the two connection pieces 4a, 4b of the connection unit 4 are correspondingly situated in their position pulled apart to the maximum as shown in FIGS. 1B and 1C, i.e. the stone catcher instrument 1 is situated in its state with the stone catcher basket 11 completely retracted into the tube 3 as shown in FIG. 1A. In an advantageous manner this is the functional state which the stone catcher instrument 1 automatically assumes, i.e. without active user manipulation.

The stone catcher instrument 1 can consequently be inserted into a body tissue canal in the state shown in FIG. 1A, with the stone catcher basket 11 completely received in the tube 3, without the user actively manipulating the two handle parts 13a, 13b in relation to each other. When the distal end of the stone catcher instrument 1 is situated at the intended site of use, i.e. in the vicinity of a stone or the like that is to be caught, the user manipulates the handle unit by moving the two handle parts 13a, 13b from their position pulled apart as shown in FIG. 9B into their position pushed together as shown in FIG. 9A. This means that the stone catcher basket 11 passes out of the tube 3 and assumes its folded-out position as shown in FIG. 2A.

As soon as a stone, particle or the like has been caught in the wire basket 11, it can be clamped therein by the user moving the front handle part 13b axially forward until the stone 12, as a result of the pulling-in movement of the wire basket that this causes, is secured in a clamping manner by the wire basket 11, i.e. the stone catcher instrument 1 is then situated in the state shown in FIGS. 3A to 3C. The prestressing action of the helical spring 9 in the connection unit 4 holds the two connection pieces 4a, 4b and, as a result, the handle parts 13a, 13b that are coupled in each case in an axially rigid manner with said connection pieces, pressed apart axially and thus ensures that the stone 12 automatically remains clamped by the wire basket 11. The stone catcher instrument 1 can then be moved out of the body tissue canal with the stone 12, captured distally in the wire basket 11 and secured in a clamping manner by said wire basket. Once again, as when inserting the stone catcher instrument 1 in the body tissue canal, it is not necessary for this purpose for the user actively to manipulate the two handle parts 13a, 13b in relation to each other. For, as with the insertion movement, the helical spring 9 of the connection unit 4 holds the stone catcher instrument 1 automatically in the desired relative position of wire pull 2 and tube, 3, when inserting (and naturally also when possibly moving out without having caught an object) in the position shown in FIG. 1A with the wire basket 11 completely retracted into the tube 3 and when moving out with the stone 12 in the position as in FIG. 3A.

FIGS. 10A to 10C illustrate a further advantage of the use of the described change-out handle system applied to the stone catcher instrument 1. The handle unit with the two handle parts 13a, 13b is designed such that the functional movement of the two handle parts 13a, 13b in relation to each other, depicted above in connection with FIGS. 9A and 9B, is preferably effected by the user actively manipulating the front handle part 13b, i.e. moving it axially, whilst the rear handle part 13a can essentially be kept stationary. The active manipulation of the front handle part 13b is made easier by the recessed handle 21 at which the user can grip the handle part 13b for manipulation. The result of this is that once the stone catcher instrument 1 has been inserted into a body tissue canal, the wire pull connected in an axially rigid manner to the rear handle part 13a, maintains its position in the body tissue canal, whilst the stone catcher basket 11 is moved out of the tube 3 and is folded open by the tube 3, coupled in an axially rigid manner to the front handle part 13b, being pulled back by the return movement of the front handle part 13b axially in relation to the body tissue canal and to the wire pull 2 and to the wire basket 11 provided at its distal end. This means that the stone catcher basket 11 remains at the site in the body tissue canal during its unfolding and its distal end, and consequently that of the stone catcher instrument 1, is not noticeably displaced axially in the body tissue canal (except for possibly a slight axial displacement of the distal end of the wire basket 11, which can be caused by the basket folding-out movement). This is illustrated in FIGS. 10A and 10B by the essentially constant distal end position or tip position and the essentially constant position of the rear connection piece 4a coupled to the rear handle part 13*a* (fixing position). Just the front connection piece 4*b* and the tube 3 coupled thereto carry out an active axial movement.

As shown in FIG. 10C, this constant distal end position (tip position) and proximal end position (fixing position) of the stone catcher instrument 1, coupled with the change-out handle system as claimed in the invention, is maintained in a substantial manner even when an object, such as the stone 12, is captured and clamped. To this end, the rear handle part 13*a* is held in the fixing position, e.g. by coupling to an external stationary unit or by fixing to the outside of the body of the patient, for example by means of plaster, or by simple securing on the side of the user. By moving the front handle part 13*b* forwards axially and consequently the front connection piece 4*b* with the tube 3 in relation to the rear connection piece 4*a* and to the rear handle part 13*a* with the wire pull 2, the wire basket 12 is pulled back into the tube 3 until it secures the captured object in a clamping manner. The prestressing of the helical spring 9 automatically provides that the captured object remains reliably clamped, even when the user then lets go of the front handle part 13*b* or the handle unit. In this case, the wire basket, as said, does not alter its axial position or at least not in a substantial manner.

This functionality illustrated in FIGS. 10A to 10C is very advantageous for simple, reliable capturing, securing and removing of stones or the like by means of the stone catcher instrument 1. For the wire basket 12 can be moved comparatively precisely at the axial height of the object to be captured and can be held at this axial height during the stone capturing movement, in contrast to such conventional stone catcher instruments where the folding open and collapsing of the stone catcher basket in the body tissue canal is accompanied at the same time by an axial movement of the wire pull and consequently also of the stone catcher basket.

The above description makes clear that and how the stone catcher instrument 1 can be removed very easily and reliably from the handle unit with the two handle parts 13*a*, 13*b*, when this is necessary, e.g. whilst the stone catcher instrument 1 is inserted into a body tissue canal. To this end, proceeding from the functional position shown in FIG. 10A or 10C, and the associated handle positions, as explained above in connection with FIGS. 9A and 9B, the handle cover tube 19 is moved into its axial end position once the latching 18 has been released, after which the two locking elements 16*a*, 16*b* are pivoted from their locking position into their unlocking position. The two connection pieces 4*a*, 4*b* can then be moved radially out of their receiving slots in the groove receiving pieces 15*a*, 15*b* and locking elements 16*a*, 16*b* until their respective annular groove latching is released. The two handle parts 13*a*, 13*b* can then be removed in the proximal direction from the stone catcher instrument 1.

Depending on the requirement, another control/manipulating unit can then be coupled to the stone catcher instrument 1, or the stone catcher instrument 1 can be pulled out of the body tissue canal at a later time without the aid of the handle unit. When the stone catcher instrument 1 is situated inside a catheter tube or endoscope, after removing the handle unit it is only possible, for example, to remove the catheter tube from the body tissue, whilst the stone catcher instrument 1 remains therein. The connection unit 4*a*, 4*b* of the stone catcher instrument 1 is designed with such a small outside diameter that the catheter tube or the endoscope can be pulled out beyond said connection unit without the connection unit 4*a*, 4*b* having to be separated from the wire pull 2 and from the tube 3 for this purpose. Where required, the handle unit with the two handle parts 13*a*, 13*b* can be recoupled to the stone catcher instrument 1 at a later time, as explained above.

The identical releasing of the coupling connection of the stone catcher instrument 1 with the handle unit is obviously possible when the stone catcher instrument 1 is situated outside a body tissue canal, for example after it has been removed from the body tissue canal and at the same time remains coupled to the handle unit. The handle unit with the two handle parts 13*a*, 13*b* can then be used, for example, for the coupling of a next stone catcher instrument.

FIGS. 11A and 11B illustrate a variant of the instrument as shown in FIGS. 1A to 10C where as the single difference, a slider 21' is provided at the corresponding front end region of the front handle part 13*b* in place of the handle recess 21 as control manipulating means. The handle cover tube 19 is provided with a corresponding front-face slot recess 40 in which the slider 21' is received in the shown position of the front handle part 13*b*, in which said front handle part is situated extensively in the handle cover tube 19. This makes a shortened design of the front handle part 13*b* in relation to the recessed handle variant possible and consequently of the entire handle unit. In addition, the shape of the slider 21' can be developed freely, e.g. according to optimum ergonomic view points.

Figure 12A:
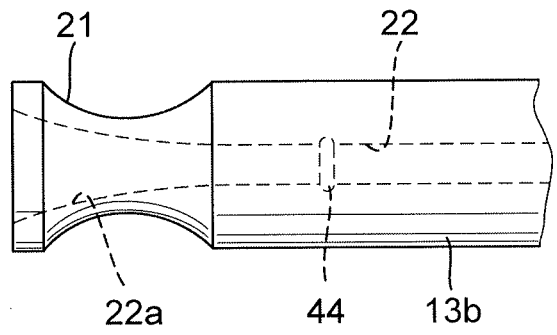
FIG. 12A shows a side view of the front handle part for a variant with a couplable entry-aiding sleeve.
Figure 12B:
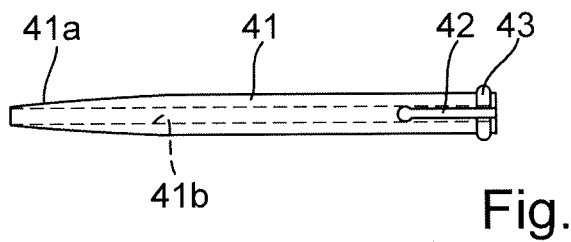
FIG. 12B shows a side view of the entry-aiding sleeve which is couplable to the handle part as in FIG. 12A.
Figure 12C:
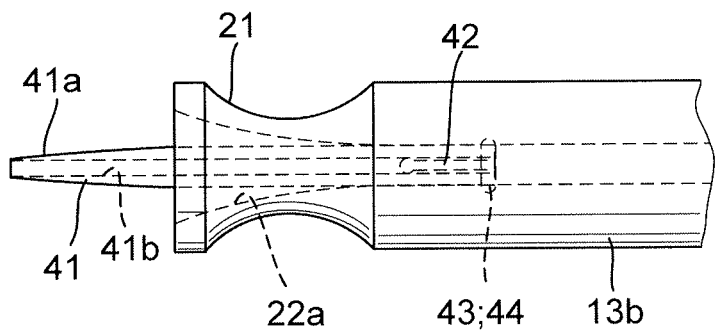
FIG. 12C shows the view of FIG. 12A with the coupled entry-aiding sleeve.

FIGS. 12A to 12C illustrate a variant where the stone catcher instrument additionally has an entry-aiding sleeve 41, which can be attached in a releasable manner on the front end region of the front handle part 13*b*, which is modified accordingly for this. For this purpose, the entry-aiding sleeve 41 has a notch 42 and a radial bead 43 at its rear end region. Corresponding to this, the opening 22 is provided with a ring-shaped latching groove 44 on the front handle part 13*b* behind its funnel-shaped widening 22*a*. The entry-aiding sleeve 43 can be pushed by way of its rear end into the funnel opening 22*a* of the front handle part 13*b* in this way. It rear end region is lightly compressed after passing the funnel-shaped widening 22*a*, which is made possible by the notch 42, and then springs back radially towards the outside in a latching manner as soon as the annular bead 43 passes into the region of the latching groove 44 in order then to take up the releasably latched position shown in FIG. 12C.

The entry-aiding sleeve 41 serves to simplify the insertion of the wire pull 2, with the wire basket 11 arranged distally thereon, and of the tube 3 surrounding the wire basket 11 into the operating canal of an endoscope and thus also in addition to protect the susceptible wire basket 11. To this end, the entry-aiding sleeve 41, once the stone catcher instrument 1 has been coupled to the handle unit 13*a*, 13*b* in the above-described manner, is pushed forward over the tube 3 as far as to the distal end of the tube 3 and the pull wire 2. To this end, it is released from its latching as in FIG. 12C under light tensile force and is then moved forward out of the front handle part 13*b*. Corresponding to its function as aiding sleeve when inserting an endoscope into the operating canal, the entry-aiding sleeve 41 has an obtuse conical front end region 41*a*. The diameter of a continuous longitudinal canal 41*b* of the entry-aiding sleeve 41 is suitably selected adapted to the outside diameter of the tube 3 in order to allow the said displacement of the entry-aiding sleeve 41 beyond the tube 3. When coupling the stone catcher instrument 1 to the handle unit 13*a*, 13*b*, the same is guided through the through-canal 41*b* of the entry-aiding sleeve 41, either before the entry-aiding sleeve 41 is latched to the front handle part 13*b* or alternatively after it has been latched thereto.

FIGS. 13A and 13B illustrate a variant of the handle unit which differs from that described previously by the additional presence of a resilient prestressing element, in this case in an exemplary manner in the form of a helical spring 45, which is received in a corresponding axial receiving bore 46 of the rear handle part 13a. At the rear end, the helical spring 45 is supported against the termination stopper 14, at its front end against a stop disk 47 which is fixed at the rear end of at least one of the guide bars 31a, 31b.

The helical spring 45 prestresses the two handle parts 13a, 13b into their extended end position as shown in FIG. 13a. In this case, the stop disk 47 abuts against a bottom surface 46a of the receiving bore 46 of the rear handle part 13a, which defines this end position. The two handle parts 13a, 13b can be pressed together out of the extended end position in opposition to the force of the helical spring 45 into their other end position as shown in FIG. 13B by the front handle part 13b being pushed into the handle cover tube 19. The helical spring 45 consequently has the identical effect as the helical spring 9 in the connection unit 4 of the stone catcher instrument 1 and consequently supports it in its function, as has been explained above, to which reference can be made. It is obvious that depending on the requirement and application, other resilient elements can be used in place of the helical spring 9 of the connection unit 4 and/or of the helical spring 45 of the handle unit 13a, 13b, it is also possible to use tension elastic elements instead of the compressed elastic elements shown an alternative, wherein, where applicable, the two elastic elements can even be provided with different effective directions and/or one of the two elastic elements can be acted upon with pressure and the other with tension.

FIG. 14 shows a further variant proceeding from the exemplary embodiment in FIGS. 13A and 13B, wherein, as the single difference, the exemplary embodiment in FIG. 14 additionally includes a variable stroke limiting element in the form of a stroke limiting longitudinal bar 48, which is fixed so as to be longitudinally adjustable as shown in a bore 47a provided in the stop disk 47. The pulled-apart end position of the two handle parts 13a, 13b is defined in this case by the stroke limiting bar 48 abutting against the bottom 46a of the spring receiving chamber 46 of the rear handle parts 13a by way of its front end 48a. This end position can be adjusted in a variable manner by adjusting the length of the stroke limiting bar 48 on the stop disk 47. This means that the handle unit 13a, 13b can be used for stone catcher instruments 1 with wire baskets 11 of different lengths and is able to be adapted in an optimum manner to the respective length of the wire basket in each case. It is obvious that such a variable stroke limiting means for the axial relative displaceability of the two handle parts 13a, 13b is also realizable in another arbitrary conventional manner as an alternative to the stroke limiting bar 48 shown. In addition, where required, the other pushed-together end position of the two handle parts 13a, 13b can also be defined in such a manner by fixing, for example, an associated stroke limiting bar of suitable length on the termination stopper 14, against which the stop disk 47 then abuts. As an alternative to this, the position and length of the stroke limiting bar 48 can be selected such that it serves to define both end positions of the handle parts 13a, 13b.

As the above description makes clear, the change-out handle system explained here makes possible a comparatively simple, convenient, releasable coupling of a stone catcher instrument which is provided for this reason with a suitable connection unit. Connection and disconnection of the stone catcher instrument to or from the handle unit with the two handle parts is effected via the connection unit with the two connection pieces without loose parts and without additional aids, such as tools. The depicted coupling connection provides for an axially rigid connection between the stone catcher instrument and the change-out handle system, more precisely between the wire pull with the rear handle part via the rear connection piece and the tube with the front handle part via the front connection piece, just through the respective positive locking of the grooves on the connection pieces with the receiving slots of the groove receiving pieces and locking elements. In this case, the locking elements also enable locking of the positive-locking connections against unintended release. In use, the stone catcher basket can be held easily in a certain axial position when folding open and collapsing for the purposes of capturing a stone or the like in a body tissue, as it is not the wire pull connected to the stone catcher basket but the tube surrounding it that is actively axially displaced. The reciprocal resilient prestressing of the two connection pieces by the helical spring or another resilient element automatically holds the stone catcher instrument in its position retracting the stone catcher basket. This enables, on the one hand, the insertion of the stone catcher instrument with its wire basket completely collapsed in the tube without active control manipulation. On the other hand, this means that the stone catcher instrument holds a captured stone automatically in a clamping manner such that even in this position of the wire basket, where required, the handle unit is able to be disconnected from the stone catcher instrument without, at the same time, losing the stone or having to ensure that it is clamped in the wire basket by means of additional control manipulation.

FIGS. 15 to 18C illustrate a further advantageous realization of the change-out handle system as claimed in the invention. This variant includes a handle unit where a first handle part 50 has a handle body made up by a lower handle shell 50A and an upper handle shell 50B that can be clipped thereon, whilst a second handle part is realized as a handle control part to be actively manipulated, i.e. to be moved by the user in the form of a slider element, which is guided by a carriage guide 56 provided on the handle body 50 so as to be axially displaceable on the same.

The slider element includes a carriage body 51 and a control head body 52, which is held so as to be transversely movable on the carriage body 51. To this end, it is inserted by way of a base part 52A through a corresponding opening 53 on the upper shell 50B onto an associated receiver 54 of the carriage body 51 and is held releasably latched in said carriage body by means of lateral clips 52B. By way of a web part 52C, the control head body 52 is guided displaceably along the slot guide 55 in the handle upper shell 50B. The carriage body 51 is guided displaceably in an axial manner in relation to the handle body 50 along the carriage guide 56 formed on the inner side of the handle body 50.

A compression spring 57 is provided between a rear end 51A of the carriage body 51 and a stop 58 integrally molded on the handle body 50 and presses the carriage body 51 into a front end position shown in FIG. 16. This is defined by a stroke limiting continuation 59 at a front end 51B of the carriage body 51 abutting against a corresponding front-side housing body stop 60. The axial length of the continuation 59 defining the stroke path can be selected to be variable, for example, at manufacture or also subsequently, such that the continuation 59 functions as a variable stroke limiting element, by way of which the stroke path of the axial relative displaceability of the carriage body 51 in relation to the handle body 50 is adjustable in a correspondingly variable manner.

In the ready assembled state, the control head body 52 protrudes out of the handle body 50 at the top side of the upper handle shell 50B by way of a mushroom head part 52D supported by the web 52C and functions as a contact element which the user contacts, for example, with a thumb in order to carry out the desired manipulation. In addition, the handle unit includes a locking pin 61, which is held in the opening 52 in the handle body 50 so as to be transversely movable between a securing and a releasing position.

For assembly, the control head body 52 is inserted by way of its base part 52A through the opening 53 and pushed forward a little such that it is held displaceably on the handle upper shell 50B. The carriage body 51 is then placed into the upper shell 50B in such a manner that the control head body 52 passes into its receiver 54 on the carriage body 51 and is fixedly clipped therein. These assembly steps are illustrated in FIG. 15 by way of an assembly arrow M2. The locking pin 61 is then inserted from below into the opening 53 of the upper shell 50B, as illustrated, by way of an assembly arrow M3, and once the compression spring 57 has been inserted, the lower shell 50A is clipped onto the upper shell 50B, as illustrated by way of an assembly arrow M1. A slot window 62 provided on the underside of the lower shell 50A is closed by releasably latching on a cover 63.

This variant of the change-out handle system is also suited in particular to the simply releasable coupling of two elongated, axially relatively displaceable functional parts of a corresponding medical instrument unit, such as a stone catcher instrument. In particular, a medical instrument unit can be coupled thereto, as is shown in more detail by way of its relevant coupling end region in FIGS. 19A to 19D. As in the case of FIGS. 1A to 3C, this can, in particular, be a stone catcher instrument 1 with a wire pull 2 and a tube 3, wherein identical reference symbols are selected for functionally equivalent components for the exemplary embodiment in FIGS. 19A to 19D to make it easier to understand. A retaining ring 64 is fixed in a rigid manner on the tube 3 just before its rear end, said retaining ring surrounding the tube 3 enlarging its diameter. In a similar manner, a retaining ring 65 is fixed in a rigid manner on the wire pull 2 just before its rear end, said retaining ring surrounding the wire pull 2 enlarging its diameter. To this end, the retaining ring 65 is fixed on a sleeve 66 with a somewhat greater axial length which, in its turn, is fixed directly on the wire pull 2. The diameter of sleeve 66 and retaining ring 65 are selected such that, in the pushed-together state as shown in FIGS. 19A and 19C, the tube 3 is pushed onto the sleeve 66 by way of it rear end and abuts against the retaining ring 65.

The medical instrument unit shown in FIGS. 19A to 19D is couplable to the change-out handle system shown in FIGS. 15 to 18C by means of the retaining rings 64, 65, which can also be designated as beading, wherein the tube is held in an axially rigid manner with the control element body 52 via its retaining ring 64 and the wire pull 2 is held in an axially rigid manner on the handle body 50 by way of its retaining ring 65. The control element body 52 and the locking pin 61, in particular, are developed suitably for this purpose.

Figure 18A:
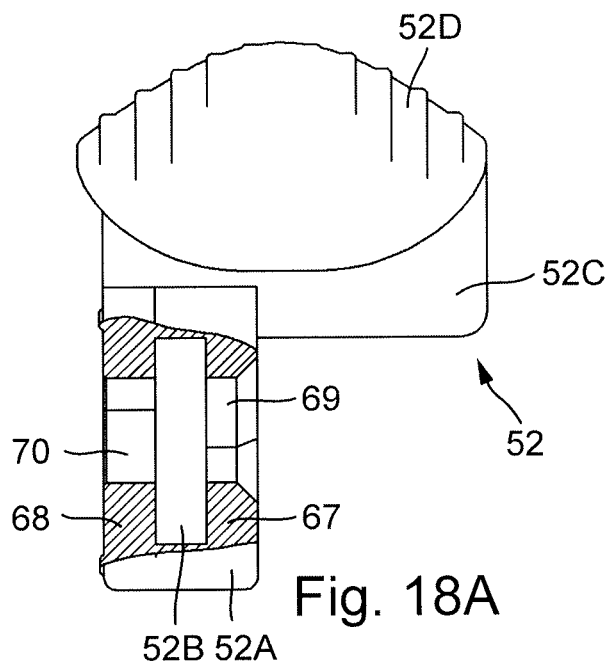
FIGS. 18A to 18C show a side view, front view or rear view of a control head body of the change-out handle system in FIG. 15.
Figure 18B:
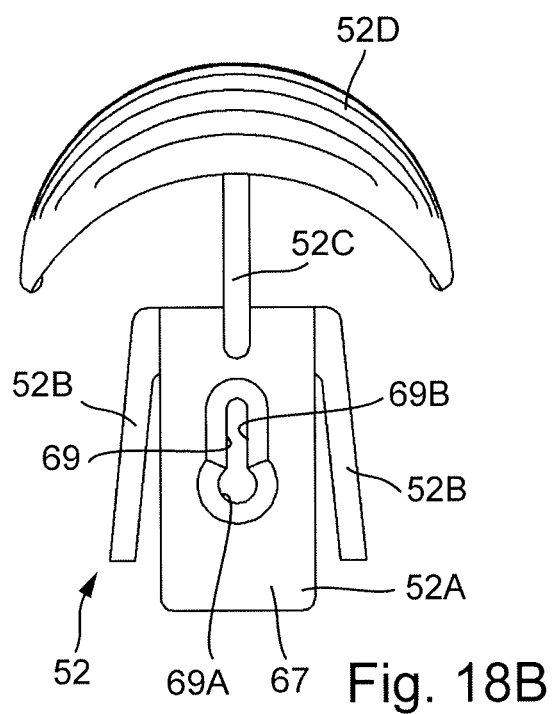
Figure 18C:
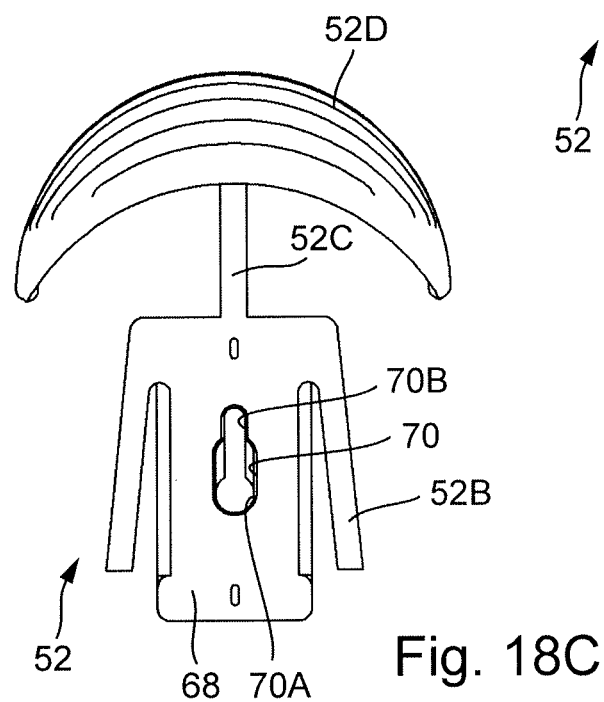

In particular, for this purpose, the base part 52A of the control element body 52 has a front wall 67 and a rear wall 68 that is spaced axially from said front wall, in each of which a slot opening 69, 70 is provided, as can be seen in more detail in the detail views in FIGS. 18A to 18C. The slot openings 69, 70 each have a larger diameter in a central region 69a, 70a than in an off-center portion 69b, 70b. In this case, the wider diameter region 69a, 70a in the front wall 67 extends with a smaller cross dimension than in the rear wall 68. Corresponding to this, the control head body 52 is clipped in its receiver 54 in such a manner that it is held on the handle body 50 so as to be transversely displaceable between a release position and a latching position and, in addition, has a central position between the two end positions.

With the medical instrument unit coupled on, the tube 3 is held on the control element body 52 so as to be axially rigid by its retaining ring 64 being secured in the region of the narrower slot opening portions 69b, 70b between front wall 67 and rear wall 68. To retain the wire pull 2 on the handle body 50 in a corresponding manner, the locking pin 61 has a similar slot opening 71 with a wider central portion and a narrowed off-center portion. As in the case of the slot openings 69, 70 of the control element body 52, the diameter of the opening on the locking pin 61 is also selected such that the relevant retaining ring 64 or 65 can pass through the larger diameter region, but is held back in contrast by the narrowed diameter region, i.e. the diameter of the respective retaining ring 64, 65 is smaller than the diameter of the opening in the central, wider region 69A, 70A and smaller than in the narrowed slot opening region 69B, 70B on the control element body 50 or at the slot opening 71 of the locking pin 61.

Like the control element body 52, the locking pin 61 is also held on the handle body 50 so as to be transversely displaceable such that, in a release position, its wider slot opening region lies in the longitudinal axis of the handle unit, along which the inserted medical instrument unit 1 extends, whilst, in a securing locking position, it holds back the retaining ring 65 and consequently the wire pull 2 by its narrower slot portion. In this last-mentioned in-use position, the wire pull 2 lies with its rear end region quasi play-free between the locking pin 61, which holds it back at its retaining ring 65, and an end stop 72 of the housing body lying behind it.

Figure 20A:
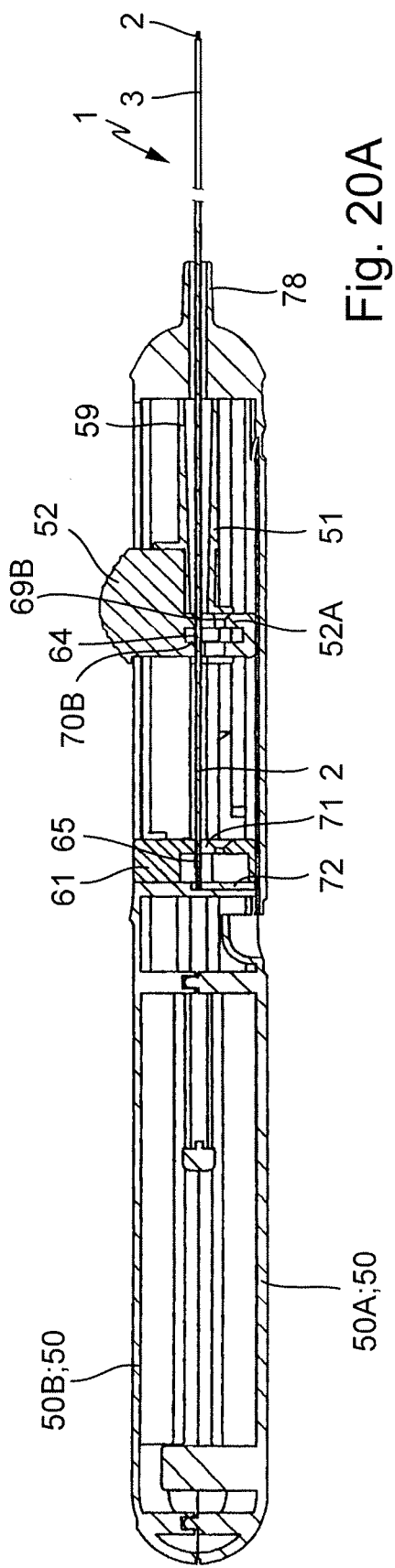
FIGS. 20A and 20B show side views of a medical stone catcher instrument with a longitudinally sectioned change-out handle system as shown in FIG. 15 in the state with the basket retracted or folded out.
Figure 20B:
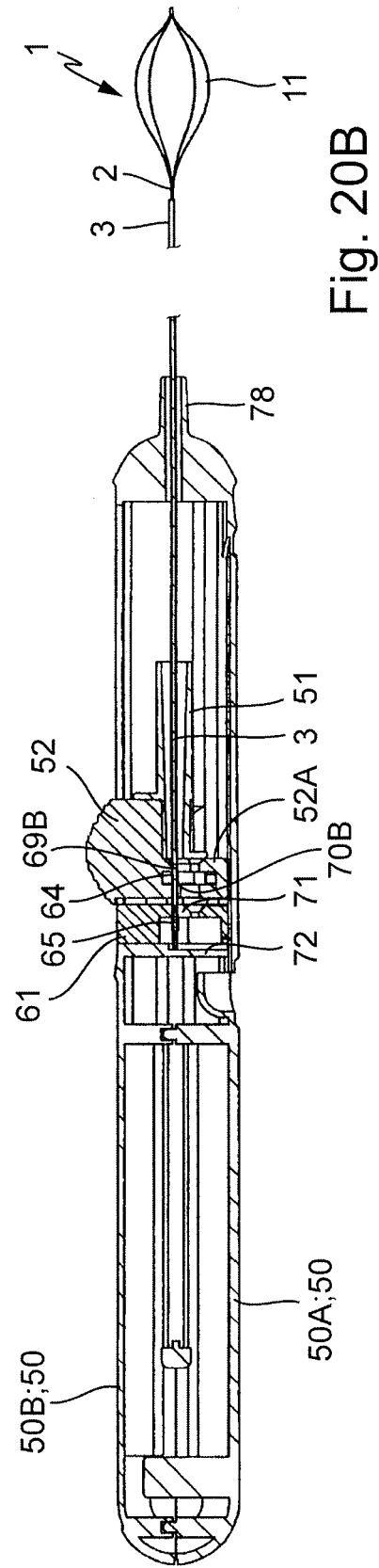

FIGS. 20A and 20B illustrate this advantageous coupling of the medical functional unit 1 with wire pull 2 and tube 3 to the change-out handle system shown in FIG. 15 by way of the example of a stone catcher instrument.

To assemble the instrument unit 1, said unit is pushed into a front-side mouth piece 78 of the handle body 50 until the tube retaining ring 64 has passed the slot opening 69 in the front wall 67 of the control element body 52, which is situated in its release position for this purpose. The control element body 52 is then moved into its central position and displaced backwards in opposition to the force of the compression spring 57, wherein, in this central position, it entrains the retaining ring 64 through the narrower slot portion 69B of the front wall 67 and at the same time pushes the entire instrument unit rearwards until the control element body 52 has reached its rear end position. In this end position, the wire pull 2 abuts against the end stop 72 on the housing body 50, and the retaining ring 65 has passed the slot opening 71 of the locking pin 61 situated in its release position and is situated directly behind said opening. The locking pin 61 is then moved transversely into its latching, securing position, and the control element body 52 is also moved transversely into its latching, securing position, in which the tube retaining ring 64 is held clamped between the narrow slot portions 69B, 70B of the two walls 67, 68 of the web part 52A of the control element body 52. It is advantageous in this case that in this axial position of instrument unit and control element body 52, the tube retaining ring 64 lies just between the two slot openings 69, 70 of the control element body 52 and consequently passes automatically into its clamped position by the transverse movement of the control element body 52. This terminates the assembly operation, and the control element body 52 can be moved back into its front initial position, in which the compression spring 57 holds it in a compressed manner.

As the above explanation makes clear, the change-out handle system makes it possible to assemble the wire instrument unit in a very simple manner without the handle body 50 having to be dismantled for this purpose. In an identical manner, simple disassembly is possible without taking the handle body 50 apart, for which purpose, after opening the cover 63, the locking pin 61 and the control element body 52 are moved transversely from below into their release position.

The instrument unit 1 is then able to be removed simply forwards out of the handle body.

FIG. 20A shows the ready assembled stone catcher instrument in its initial position, in which the control element body 52 is situated in its front end position and the wire basket 11 provided at the distal end of the wire pull 2 is completely retracted into the tube 3. FIG. 20B shows the instrument in the position in which the control element body 52 is pressed back into its rear end position. In the case of this return movement, the control element body 52 entrains the coupled tube 3, whilst the wire pull 2 remains stationary. The result of this is that the tube 3 pulls back at the distal end region and releases the wire basket 11 into its unfolded state.

The properties and advantages of the instrument as shown in FIGS. 15 to 20B, moreover, are analogous to those specified above for the instrument shown in FIGS. 1A to 14, to which reference can be made.

Figure 21:
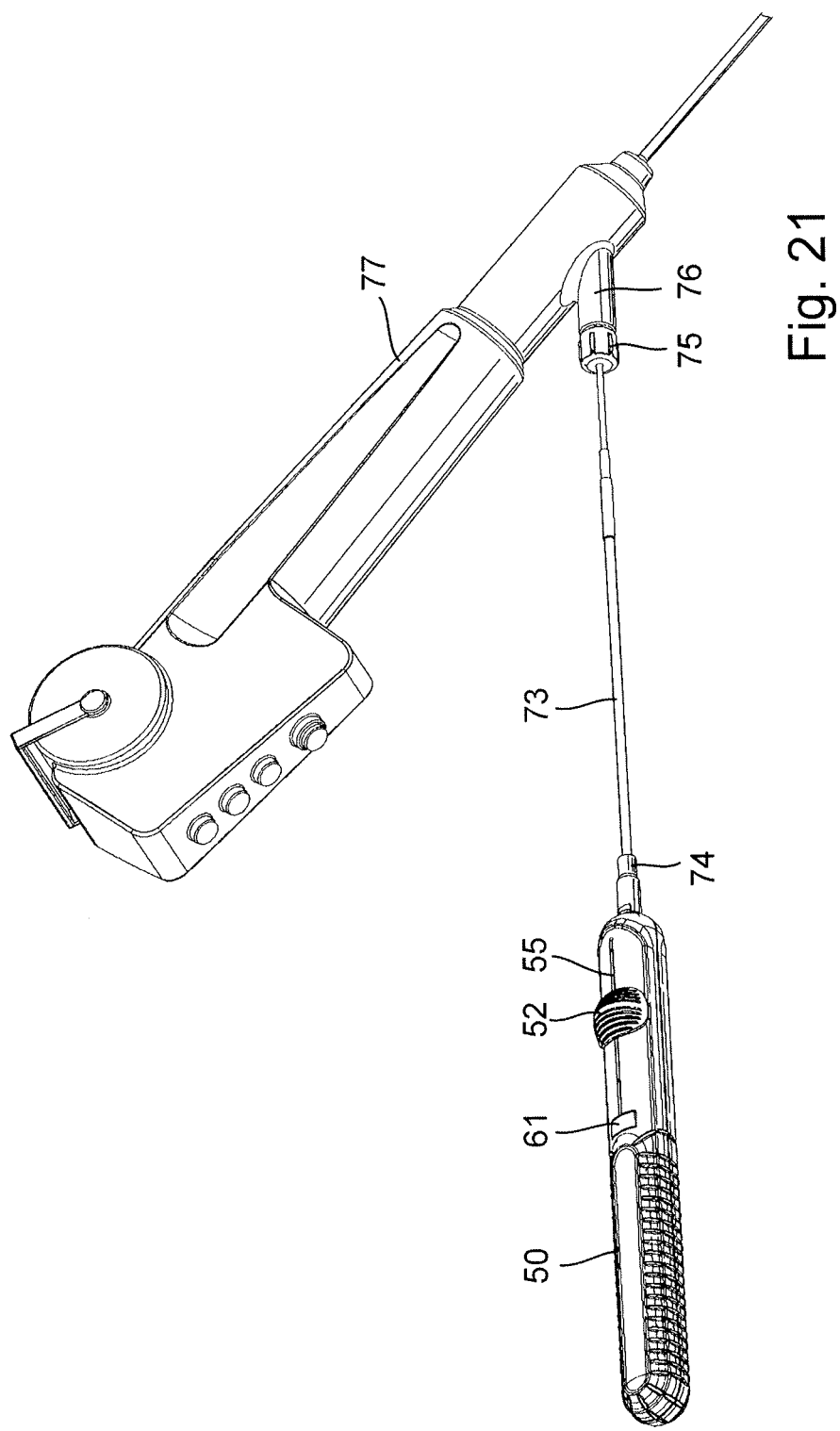
FIG. 21 shows a perspective view of a handle-side part of an endoscope with a medical instrument corresponding to FIGS. 20A and 20B coupled to an endoscopy handle body.

FIG. 21 shows an advantageous coupling possibility of the stone catcher instrument in FIGS. 20A and 20B to an endoscope. A telescopic adapter sleeve 73 is provided for this purpose, said telescopic adapter sleeve being provided at the one end with a connection 74 matching the housing body mouth piece 80 and at the other end with a Luer connection 75, by way of which it can be coupled to a corresponding connection 76 of a conventional type of endoscope handle part 77. The length of the adapter sleeve 73 is variably adjustable in a telescopic manner.

It is obvious that the change-out handle system as claimed in the invention can be realized, aside from the embodiments shown, in many further embodiments by way of which the advantages mentioned above with respect to the examples shown can be achieved completely, or in any case in part, depending on the system realization. In particular, the change-out handle system as claimed in the invention can obviously also be used for other medical instruments which have two elongated, axially relatively displaceable functional parts, which are to be coupled releasably to a handle system, such as, for example, medical instruments which, like the depicted stone catcher instrument, have a wire pull and a tube which surrounds it and is axially displaceable in relation thereto, wherein, instead of the stone catcher basket, another functional element is arranged at the distal end of the instrument, for example, a cutting element, a filtering element etc. Also as an alternative to the disk-shaped or slider-like or pin-like closing elements shown, depending on the system design, other conventional types of locking elements can be used, for example those that are based on a valve mechanism. The most important fact, in this respect, is purely the locking function securing against unintended release of the axially rigid coupling connection between wire pull or tube and the relevant handle part. In addition, it is obvious that the two elongated, axially relatively displaceable functional parts of a medical instrument that can be coupled releasably to the change-out handle system as claimed in the invention do not forcibly have to be an elongated wire and a tube surrounding said wire, as shown, but can also be two other functional parts, depending on the type of medical instrument, for example, two axially relatively displaceable functional wires which are arranged next to each other or coaxially. In addition, it is obvious that the change-out handle system as claimed in the invention is not restricted to the area of application of medical instruments, but can be applied in an identical manner in other areas where there is the requirement to be able to couple two elongated, axially relatively displaceable functional parts releasably to a control handle unit.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all changes and modifications as fall within the spirit and scope of the invention, as defined by the appended claims, and equivalents thereof.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A change-out handle system configured for releasably coupling two elongated, axially relatively displaceable functional parts, comprising:
   a first and a second handle part which are arranged so as to be axially relatively displaceable;
   a first axially rigid coupler, the first coupler providing a releasable, axially rigid coupling of a first one of the two functional parts to the first handle part; and
   a second axially rigid coupler, the second coupler providing a releasable, axially rigid coupling of the second one of the two functional parts to the second handle part,
   wherein
      the second handle part has an opening for passing through at least the first of the two functional parts, and
      the first and second handle parts are configured for one-handed active manipulation wherein a portion of the first handle part, proximally arranged relative to a portion of the second handle part, is gripped, and the portion of the second handle part is axially displaced in order to axially displace the functional parts relative to one another, and
   wherein the first coupler has a first coupling element on the first handle part, by way of which a first counter coupling element is releasably coupleable to a rear end region of the first functional part.

2. A change-out handle system configured for releasably coupling two elongated, axially relatively displaceable functional parts, comprising:
   a first and a second handle part which are arranged so as to be axially relatively displaceable;
   a first axially rigid coupler, the first coupler providing a releasable, axially rigid coupling of a first one of the two functional parts to the first handle part; and
   a second axially rigid coupler, the second coupler providing a releasable, axially rigid coupling of the second one of the two functional parts to the second handle part,
   wherein
      the second handle part has an opening for passing through at least the first of the two functional parts, and
      the first and second handle parts are configured for one-handed active manipulation wherein a portion of the first handle part, proximally arranged relative to a portion of the second handle part, is gripped, and the portion of the second handle part is axially displaced in order to axially displace the functional parts relative to one another, and
   wherein the second coupler has a second coupling element, by way of which a second counter coupling element is releasably coupleable to a rear end region of the second functional part.

3. The change-out handle system as claimed in claim 1, wherein at least one of the first coupling element and a second coupling element includes a respective groove or groove receiver for forming a positive-locking coupling element/counter coupling element pair with a respectively corresponding groove receiver or groove as counter coupling element or a respective slot opening for forming a positive-locking pair with a respective retaining ring element or bead element.

4. The change-out handle system as claimed in claim 3, wherein a securing device for the respective groove/groove receiver pair includes a manipulatable locking element which locks the groove/groove receiver connection against release and unlocks it for release.

5. The change-out handle system as claimed in claim 1, further comprising a variable stroke limiting element for the variable adjustment of a stroke path of the axial relative displaceability of the first and second handle part.

6. The change-out handle system as claimed in claim 1, further comprising a resilient prestressing element which acts in the axial direction between the two handle parts.

7. The change-out handle system as claimed in claim 1, wherein the second handle part includes a handle control part which is to be actively manipulated.

8. The change-out handle system as claimed in claim 1, wherein the first handle part forms a rear handle part and the second handle part forms a front handle part.

9. The change-out handle system as claimed in claim 8, wherein the opening widens outwards in the shape of a funnel in a front end region of the front handle part.

10. The change-out handle system as claimed in claim 8, further comprising a handle cover tube, which is guided in an axially displaceable manner on the rear handle part and releases a front end portion of the rear handle part and a rear end portion of the front handle part in an axially rear end position and covers them in an axially front end position.

11. The change-out handle system as claimed in claim 10, further comprising a latch for the releasable latching of the handle cover tube in its axially front end position.

12. The change-out handle system as claimed in claim 7, wherein the first handle part forms a handle body with a carriage guide and the handle control part is realized as a slider element which is guided on the handle body in an axially displaceable manner by the carriage guide.

13. The change-out handle system as claimed in claim 12, wherein the slider element includes a carriage body and a control element body, which is held so as to be transversely movable on the carriage body and forms the associated securing device for securing the coupling connection between the second handle part and the second functional part, wherein it is transversely displaceable between a latching slide control position and a position disengaging the securing function.

14. The change-out handle system according to claim 1, wherein the two elongated, axially relatively displaceable functional parts comprise:
  a first elongated functional part with a first axially rigid counter coupling element provided on a rear end region, the first counter coupling element providing a releasable, axial rigid coupling to the first handle part of the change-out handle system; and
  a second elongated functional part, which is axially relatively displaceable with respect to the first functional part with a second axially rigid counter coupling element provided on a rear end region, the second counter coupling element providing a releasable, axially rigid coupling to the second handle part of the change-out handle system, wherein the first counter coupling element includes a first connection piece provided on the first functional part and the second counter coupling element includes a second connection piece provided on the second functional part, and
a resilient element directly rests at one end against the first connection piece and at another end against the second connection piece, the resilient element acting in the axial direction between the two connection pieces of the medical instrument unit.

15. The change-out handle system as claimed in claim 14, wherein the rear end regions of the first and second elongated functional parts including the first and second counter coupling elements are configured with an outside diameter small enough to allow a catheter tube or endoscope to be pulled over said rear end regions of the first and second elongated functional parts.

16. The change-out handle system as claimed in claim 14, wherein the two functional parts are a wire pull and a tube surrounding said wire pull.

17. The change-out handle system as claimed in claim 16, wherein the wire pull forms the first functional part and the tube forms the second functional part.

18. The change-out handle system as claimed in claim 16, wherein the two functional parts form a stone catching basket instrument unit.

19. The change-out handle system as claimed in claim 16, further comprising an entry-aiding sleeve, which surrounds the tube, in a rest position is attached releasably on the front handle part and is displaceable out of the rest position forward as far as the distal end region of the wire pull and tube into an entry-aiding position.

20. A medical instrument with a change-out handle system and a medical instrument unit, wherein the change-out handle system is configured for releasably coupling two elongated, axially relatively displaceable functional parts and comprises:
  a first and a second handle part which are arranged so as to be axially relatively displaceable;
  a first axially rigid coupler providing a releasable, axially rigid coupling of a first one of the two functional parts to the first handle part; and
  a second axially rigid coupler providing a releasable, axially rigid coupling of the second one of the two functional parts to the second handle part,
  wherein the second handle part has an opening for passing through at least the first of the two functional parts, and the first and second handle parts are configured for one-handed active manipulation wherein a portion of the first handle part, proximally arranged relative to a portion of the second handle part, is gripped, and the portion of the second handle part is axially displaced in order to axially displace the functional parts relative to one another, and
  wherein the medical instrument unit comprises:
    a first elongated functional part with a first axially rigid counter coupling element provided on a rear end region, the first counter coupling element providing a releasable, axial rigid coupling to the first handle part of the change-out handle system; and
    a second elongated functional part, which is axially relatively displaceable with respect to the first functional part with a second axially rigid counter coupling element provided on a rear end region, the second counter coupling element providing a releasable, axially rigid coupling to the second handle part of the change-out handle system.

21. The medical instrument as claimed in claim 20, wherein it is an endoscopy instrument with an endoscopy handle body, wherein the endoscopy instrument has a telescopic adapter sleeve for coupling the medical instrument unit to the endoscopy handle body.

22. A medical instrument with a change-out handle system and a medical instrument unit, wherein the change-out handle system is configured for releasably coupling two elongated, axially relatively displaceable functional parts and comprises:
- a first and a second handle part which are arranged so as to be axially relatively displaceable;
- a first axially rigid coupler providing a releasable, axially rigid coupling of a first one of the two functional parts to the first handle part; and
- a second axially rigid coupler providing a releasable, axially rigid coupling of the second one of the two functional parts to the second handle part,
wherein the second handle part has an opening for passing through at least the first of the two functional parts, and wherein the medical instrument unit is a stone catching basket instrument unit and comprises:
- a first elongated functional part with a first axially rigid counter coupling element provided on a rear end region, the first counter coupling element providing a releasable, axial rigid coupling to the first handle part of the change-out handle system; and
- a second elongated functional part, which is axially relatively displaceable with respect to the first functional part with a second axially rigid counter coupling element provided on a rear end region, the second counter coupling element providing a releasable, axially rigid coupling to the second handle part of the change-out handle system,
wherein a wire pull forms the first elongated functional part and a tube surrounding the wire pull forms the second elongated functional part, the tube coupled to the second handle part being actively manipulated so as to be axially displaced relative to the wire pull via the second handle part, while the wire pull coupled to the first handle part remains stationary.

23. The change-out handle system as claimed in claim 1, wherein at least one of the first and the second coupler has an associated manipulatable securing device for securing the associated coupling connection between functional part and handle part.

\* \* \* \* \*